US011034989B2

(12) United States Patent
Allen et al.

(10) Patent No.: US 11,034,989 B2
(45) Date of Patent: Jun. 15, 2021

(54) SYNTHESIS OF LONG NUCLEIC ACID SEQUENCES

(71) Applicant: Integrated DNA Technologies, Inc., Coralville, IA (US)

(72) Inventors: Shawn Allen, Williamsburg, IA (US); Stephen Gunstream, Iowa City, IA (US); Scott Rose, Coralville, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 362 days.

(21) Appl. No.: 15/591,783

(22) Filed: May 10, 2017

(65) Prior Publication Data

US 2017/0260558 A1   Sep. 14, 2017

Related U.S. Application Data

(63) Continuation of application No. 14/865,127, filed on Sep. 25, 2015, now Pat. No. 9,670,517, which is a continuation of application No. 13/742,959, filed on Jan. 16, 2013, now abandoned.

(60) Provisional application No. 61/587,073, filed on Jan. 16, 2012.

(51) Int. Cl.
*C12P 19/34* (2006.01)
*C12Q 1/6844* (2018.01)
*C12N 15/10* (2006.01)

(52) U.S. Cl.
CPC .......... *C12P 19/34* (2013.01); *C12N 15/1068* (2013.01); *C12Q 1/6844* (2013.01); *B01J 2219/00596* (2013.01); *B01J 2219/00722* (2013.01)

(58) Field of Classification Search
CPC ............... C12P 19/34; C12Q 1/6844; B01J 2219/00596; B01J 2219/00722; C12N 15/1068
See application file for complete search history.

(56) References Cited

U.S. PATENT DOCUMENTS

| | | | |
|---|---|---|---|
| 6,040,439 A | 3/2000 | Hayakawa et al. | |
| 7,482,119 B2 | 1/2009 | Parker et al. | |
| 7,691,316 B2 | 4/2010 | Ngo et al. | |
| 7,776,532 B2 | 8/2010 | Gibson et al. | |
| 8,435,736 B2 | 5/2013 | Gibson et al. | |
| 8,697,408 B2 | 4/2014 | Kucera et al. | |
| 2009/0317873 A1 | 12/2009 | Govindarajan et al. | |
| 2010/0216648 A1 | 8/2010 | Staehler et al. | |
| 2011/0172127 A1 | 7/2011 | Jacobson et al. | |
| 2014/0187447 A1 | 7/2014 | Kucera et al. | |
| 2016/0333340 A1 | 11/2016 | Wu | |

OTHER PUBLICATIONS

Shao et al. DNA assembler, an in vivo genetic method for rapid construction of biochemical pathways. Nucleic Acids Research (2009) vol. 37, No. 2, e16, , pp. 1-10, published online, Dec. 12, 2008. (Year: 2009).*
Caruthers et al., "Chemical synthesis of deoxyoligonucleotides by the phosphoramidite method" Methods in Enzymology (1987) 154:287-313.
Tian et al., "Advancing high-throughput gene synthesis technology" Mol. BioSyst (2009) 5, 714-722.
Gao, X. et al., "Thermodynamically balanced inside-out (TBIO) PCR-based gene synthesis: a novel method of primer design for high-fidelity assembly of longer gene sequences" Nucleic Acids Research (2003) 31(22):e143.
Sierzchala, A.B. et al., "Solid-Phase Oligodeoxynucleotide Synthesis: A Two-Step Cycle Using Peroxy Anion Deprotection" JACS (2003) 125:13427-13441.
Azhayev, A.V. et al., "Amide group assisted 3'-dephosphorylation of oligonucleotides synthesized on universal A-supports" Tetrahedron (2001) 57:4977-4986.
Kozlov, I.A. et al., "Significant improvement of quality for long oligonucleotides by using controlled pore glass with large pores" Nucleosides, Nucleotides and Nucleic Acids (2005) 24(5-7):1037-1041.
Czar, M.J. et al., "Gene synthesis demystified" Trends in Biotechnology (2008) 27(2):63-72.
Damha, M.J. et al., "An improved procedure for derivatization of controlled-pore glass beads for solid-phase oligonucleotide synthesis" Nucleic Acids Research (1990) 18(13):3813-3821.
Bang, D. et al. "Gene synthesis by circular assembly amplification" Nature Methods (2008) 5:37-39.
Carr, P.A. et al., "Protein-mediated error correction for de novo DNA synthesis" Nucleic Acids Research (2004) 32, e162.
Yehezkel, T.B. et al., "De novo DNA synthesis using single molecule PCR" Nucleic Acids Research (2008) 36(17): e107.
Gibson, D.G. et al., "Complete Chemical Synthesis, Assembly, and Cloning of a Mycoplasma genitalium Genome" Science (2008) 319:1215-1220.
Gibson, D.G. et al., "Enzymatic assembly of DNA molecules up to several hundred kilobases" Nature Methods (2009) 6(5):343-347.
Kodumal, S.J. et al., "Total synthesis of long DNA sequences: Synthesis of a contiguous 32-kb polyketide synthase gene cluster" PNAS (2004) 101(44):15573-15578.
Villalobos, A. et al., "Gene Designer: a synthetic biology tool for constructing artificial DNA segments" BMC Bioinformatics (2006) 7:285.
Larionov, V. et al., "Specific cloning of human DNA as yeast artificial chromosomes by transformation-associated recombination" PNAS (1996) 93:491-496.
Shevchuk et al. "Construction of long DNA molecules using long PCR-based fusion of several fragments simultaneously." Nucleic Acids Research (2004) vol. 32, No. 2 e19, pp. 1-12.

* cited by examiner

*Primary Examiner* — David C Thomas
(74) *Attorney, Agent, or Firm* — John A. Petravich; David J. Youngkin

(57) ABSTRACT

The invention provides methods for the synthesis of long oligonucleotides, genes and gene fragments. The methods include the manufacture of genes or gene fragments that can be then inserted into a variety of vectors.

10 Claims, 9 Drawing Sheets

Specification includes a Sequence Listing.

Design 1 = Long gene sub-blocks
    Gene sub-block length: 115-185 bases
    TSP overlaps: 70°C Tm Design 2 = Gene sub-blocks limited to 125 bases
    Gene sub-block length: 54-125 bases
    TSP overlaps: 70°C Tm Design 3 = 100 base gene sub-blocks
    Gene sub-block length: 80-124 bases (all are 100 bases except for last sub-block)
    TSP overlaps: 50 bases

SEQUENCE LISTING

```
<160> NUMBER OF SEQ ID NOS: 92

<210> SEQ ID NO 1
<211> LENGTH: 935
<212> TYPE: DNA
<213> ORGANISM: Artificial Sequence
<220> FEATURE:
<223> OTHER INFORMATION: Synthetic gene block

<400> SEQUENCE: 1
cgacactgct cgatccgctc gcaccaaatc cagatgacac agagtccgtc ctcgctttct      60
gcgtccctgg gcgatcgtgt aaccattaca tgtcaggcta gtcgcggcat cggaaaagac     120
ttaaattggt accagcagaa agcgggcaaa gcccctaaac tgctggtgag cgatgccagc     180
acattggagg gcggcgttcc gtcacgtttc agtggtagcg gcttccatca aaatttcagc     240
ttaaccatct ccagtctgca ggccgaggat gtggctacct atttctgcca gcagtatgaa     300
actttcggcc agggaaccaa agtcgatatt aaaaggtcga cggtcgcgcc gagcgtgttt     360
attttcccgc cgtctgatga acagctgaaa tcaggcaccg catcggtggt ttgcctgctg     420 aacaatttt atccgcgtga agcgaaagtt cagtggaaag tggataacgc cctgcagagc     480
ggtaattcgc aagaaagcgt caccgaacaa gattctaaag acagtacgta ctccctgagc     540
tctaccctga cgctgtcaaa agcagattac gaaaaacata aagtgtacgc ttgcgaagtt     600
acccaccaag gcctgagttc cccggttacg aaatccttca ccgtggcga atgttaagct      660 ggggatcctc tagaggttga ggtgatttta tgaagaaaaa cattgcgttt ctgctggcga     720
gcatgtttgt gttctctatc gccaccaatg cgtatgccct cgagcaagtg caattggtcc     780
agtcgggcgc ggaagttaag aaaccggggg cctctgtgaa agtctcctgc aaagcctctg     840
gttatacgtt tacaggctac tatatgcact gggtgcgtca agccccgggt caaggtctgg     900
agtggatggg ttggattaac ccgaactccg gtggt                                935

<210> SEQ ID NO 2
<211> LENGTH: 1155
<212> TYPE: DNA
<213> ORGANISM: Artificial Sequence
<220> FEATURE:
<223> OTHER INFORMATION: Synthetic gene block

<400> SEQUENCE: 2
cgacactgct cgatccgctc gcaccaaatc cagatgacac agagtccgtc ctcgctttct      60
gcgtccctgg gcgatcgtgt aaccattaca tgtcaggcta gtcgcggcat cggaaaagac     120
ttaaattggt accagcagaa agcgggcaaa gcccctaaac tgctggtgag cgatgccagc     180
acattggagg gcggcgttcc gtcacgtttc agtggtagcg gcttccatca aaatttcagc     240
ttaaccatct ccagtctgca ggccgaggat gtggctacct atttctgcca gcagtatgaa     300
actttcggcc agggaaccaa agtcgatatt aaaaggtcga cggtcgcgcc gagcgtgttt     360
attttcccgc cgtctgatga acagctgaaa tcaggcaccg catcggtggt ttgcctgctg     420 aacaatttt atccgcgtga agcgaaagtt cagtggaaag tggataacgc cctgcagagc     480
ggtaattcgc aagaaagcgt caccgaacaa gattctaaag acagtacgta ctccctgagc     540
```

```
tctaccctga cgctgtcaaa agcagattac gaaaaacata aagtgtacgc ttgcgaagtt        600
acccaccaag gcctgagttc cccggttacg aaatccttca accgtggcga atgttaagct        660
ggggatcctc tagaggttga ggtgatttta tgaagaaaaa cattgcgttt ctgctggcga        720
gcatgtttgt gttctctatc gccaccaatg cgtatgccct cgagcaagtg caattggtcc        780
agtcgggcgc ggaagttaag aaaccggggg cctctgtgaa agtctcctgc aaagcctctg        840
gttatacgtt tacaggctac tatatgcact gggtgcgtca agccccgggt caaggtctgg        900
agtggatggg ttggattaac ccgaactccg gtggtaccaa ctatgcgcag aaattccagg        960
gtcgcgtcac gatgactcgc gacacgtcaa ttagtaccgc gtacatggag ttatcgcgtt       1020
tacgtagtga cgacaccgcc gtatactact gtgcgcgtgc tcagaaacgc ggccgttctg       1080
aatgggcgta cgcacattgg ggtcaaggca ccctggtgac cgtgagtagt ggatcgacga       1140
gagcagcgcg actgg                                                        1155

<210> SEQ ID NO 3
<211> LENGTH: 189
<212> TYPE: DNA
<213> ORGANISM: Artificial Sequence
<220> FEATURE:
<223> OTHER INFORMATION: synthetic oligonucleotide

<400> SEQUENCE: 3
cgacactgct cgatccgctc gcaccaaatc cagatgacac agagtccgtc ctcgctttct         60
gcgtccctgg gcgatcgtgt aaccattaca tgtcaggcta gtcgcggcat cggaaaagac        120
ttaaattggt accagcagaa agcgggcaaa gcccctaaac tgctggtgag cgatgccagc        180
acattggag                                                                189

<210> SEQ ID NO 4
<211> LENGTH: 162
<212> TYPE: DNA
<213> ORGANISM: Artificial Sequence
<220> FEATURE:
<223> OTHER INFORMATION: synthetic oligonucleotide

<400> SEQUENCE: 4
ctggtgagcg atgccagcac attggagggc ggcgttccgt cacgtttcag tggtagcggc         60
ttccatcaaa atttcagctt aaccatctcc agtctgcagg ccgaggatgt ggctacctat        120
ttctgccagc agtatgaaac tttcggccag ggaaccaaag tc                           162

<210> SEQ ID NO 5
<211> LENGTH: 189
<212> TYPE: DNA
<213> ORGANISM: Artificial Sequence
<220> FEATURE:
<223> OTHER INFORMATION: synthetic oligonucleotide

<400> SEQUENCE: 5
gcagtatgaa actttcggcc agggaaccaa agtcgatatt aaaaggtcga cggtcgcgcc         60
gagcgtgttt attttcccgc cgtctgatga acagctgaaa tcaggcaccg catcggtggt        120
ttgcctgctg aacaatttt atccgcgtga agcgaaagtt cagtggaaag tggataacgc        180
cctgcagag                                                                189

<210> SEQ ID NO 6
<211> LENGTH: 189
<212> TYPE: DNA
```

<213> ORGANISM: Artificial Sequence
<220> FEATURE:
<223> OTHER INFORMATION: synthetic oligonucleotide

<400> SEQUENCE: 6

```
gttcagtgga aagtggataa cgccctgcag agcggtaatt cgcaagaaag cgtcaccgaa      60
caagattcta aagacagtac gtactccctg agctctaccc tgacgctgtc aaaagcagat     120
tacgaaaaac ataaagtgta cgcttgcgaa gttacccacc aaggcctgag ttccccggtt     180
acgaaatcc                                                             189
```

<210> SEQ ID NO 7
<211> LENGTH: 174
<212> TYPE: DNA
<213> ORGANISM: Artificial Sequence
<220> FEATURE:
<223> OTHER INFORMATION: Synthetic oligonucleotide

<400> SEQUENCE: 7

```
ccaaggcctg agttccccgg ttacgaaatc cttcaaccgt ggcgaatgtt aagctgggga      60
tcctctagag gttgaggtga ttttatgaag aaaaacattg cgtttctgct ggcgagcatg     120
tttgtgttct ctatcgccac caatgcgtat gccctcgagc aagtgcaatt ggtc           174
```

<210> SEQ ID NO 8
<211> LENGTH: 185
<212> TYPE: DNA
<213> ORGANISM: Artificial Sequence
<220> FEATURE:
<223> OTHER INFORMATION: Synthetic oligonucleotide

<400> SEQUENCE: 8

```
cgtatgccct cgagcaagtg caattggtcc agtcgggcgc ggaagttaag aaaccggggg      60
cctctgtgaa agtctcctgc aaagcctctg gttatacgtt tacaggctac tatatgcact     120
gggtgcgtca gccccgggt caaggtctgg agtggatggg ttggattaac ccgaactccg     180
gtggt                                                                 185
```

<210> SEQ ID NO 9
<211> LENGTH: 122
<212> TYPE: DNA
<213> ORGANISM: Artificial Sequence
<220> FEATURE:
<223> OTHER INFORMATION: Synthetic oligonucleotide

<400> SEQUENCE: 9

```
gggttggatt aacccgaact ccggtggtac caactatgcg cagaaattcc agggtcgcgt      60
cacgatgact cgcgacacgt caattagtac cgcgtacatg gagttatcgc gtttacgtag     120
tg                                                                    122
```

<210> SEQ ID NO 10
<211> LENGTH: 161
<212> TYPE: DNA
<213> ORGANISM: Artificial Sequence
<220> FEATURE:
<223> OTHER INFORMATION: Synthetic oligonucleotide

<400> SEQUENCE: 10

```
taccgcgtac atggagttat cgcgtttacg tagtgacgac accgccgtat actactgtgc      60
gcgtgctcag aaacgcggcc gttctgaatg ggcgtacgca cattgggtc aaggcaccct     120 ggtgaccgtg agtagtggat cgacgagagc agcgcgactg g                         161
```

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
cgacactgct cgatccgctc gcacc                                          25

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
ccagtcgcgc tgctctcgtc gatcc                                          25

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 13
accaccggag ttcgggttaa tccaacc                                        27

<210> SEQ ID NO 14
<211> LENGTH: 480
<212> TYPE: DNA
<213> ORGANISM: Artificial Sequence
<220> FEATURE:
<223> OTHER INFORMATION: Synthetic oligonucleotide

<400> SEQUENCE: 14
cgacactgct cgatccgctc gcacctttct ggcatgaggt cactgacagc cctctggaca    60
acacagctta tttattggtc tctcattctc ccatccccac tcctcctttc ttccctctct   120
ccaccagagc gatggcgtca ccggcccatc ctccaagccg gactgccggc aaatgcctcc   180
acagtggtcg gaggagacgt agagtttgtc tgcaaggttt acagtgatgc ccagccccac   240
atccagtgga tcaagcacgt ggaaaagaac ggcagtaaat acgggcccga cgggctgccc   300
tacctcaagg ttctcaaggt gaggactttc tgaatctaaa ggtacccaca actgggtct   360 ccttcatggg tttggccaca ggttctttga tttcctgttg gagttgagag aggatgattc   420 tctttttga ctagccagca gagagtgttc taagggatc gacgagagca gcgcgactgg    480

<210> SEQ ID NO 15
<211> LENGTH: 509
<212> TYPE: DNA
<213> ORGANISM: Artificial Sequence
<220> FEATURE:
<223> OTHER INFORMATION: Synthetic oligonucleotide

<400> SEQUENCE: 15
cgacactgct cgatccgctc gcaccgcacc tgtacgatca ctgaactgca gaatctggga    60
tgttaaccag aagaccttct atctgaggaa caaccaacta gttgctggat acttgcaagg   120
accaaatgtc aatttagaag aaaagttcga catgtccttt gtagaaggac atgaaagtaa   180

```
tgacaaaata cctgtggcct tgggcctcaa ggaaaagaat ctgtacctgt cctgcgtgtt      240
gaaagatgat gaacccactc tacagctgga ggctgtaaat cccaaaaatt acccaaagag      300
gaagatggaa aagcgatttg tcttcaacaa gatagattca ggcccaacca catcatttga      360
gtctgcccag ttccccaact ggttcctctg cacagcgatg gaagctgacc agcccgtcag      420
cctcaccaat atgcctgacg aaggcgtcat ggtcaccaaa ttctacatgc aatttgtgtc      480
ttccggatcg acgagagcag cgcgactgg                                         509

<210> SEQ ID NO 16
<211> LENGTH: 520
<212> TYPE: DNA
<213> ORGANISM: Artificial Sequence
<220> FEATURE:
<223> OTHER INFORMATION: Synthetic oligonucleotide

<400> SEQUENCE: 16
cgacactgct cgatccgctc gcacccatat ggccaagctg accagcgccg ttccggtgct       60
caccgcgcgc gacgtcgccg gagcggtcga gttctggacc gaccggctcg ggttctcccg      120
ggacttcgtg gaggacgact cgccggtgt ggtccgggac gacgtgaccc tgttcatcag      180
cgcggtccag gaccaggtaa gacgcaattc tgctgtgcac gtgccaatgc cgctgccccc      240
cagcgcattg gctcaccatc gccatcgcca ttgctgctgc aggtggtgcc ggacaacacc      300
ctggcctggg tgtgggtgcg cggcctggac gagctgtacg ccgagtggtc ggaggtcgtg      360
tccacgaact tccgggacgc ctccgggccg gccatgaccg agatcggcga gcagccgtgg      420
gggcgggagt tcgccctgcg cgacccggcc ggcaactgcg tgcacttcgt ggccgaggag      480
caggactaag gatccggatc gacgagagca gcgcgactgg                            520

<210> SEQ ID NO 17
<211> LENGTH: 184
<212> TYPE: DNA
<213> ORGANISM: Artificial Sequence
<220> FEATURE:
<223> OTHER INFORMATION: Synthetic oligonucleotide

<400> SEQUENCE: 17
cgacactgct cgatccgctc gcacctttct ggcatgaggt cactgacagc cctctggaca       60
acacagctta tttattggtc tctcattctc ccatccccac tcctcctttc ttccctctct      120
ccaccagagc gatggcgtca ccggcccatc ctccaagccg gactgccggc aaatgcctcc      180
acag                                                                   184

<210> SEQ ID NO 18
<211> LENGTH: 183
<212> TYPE: DNA
<213> ORGANISM: Artificial Sequence
<220> FEATURE:
<223> OTHER INFORMATION: Synthetic oligonucleotide

<400> SEQUENCE: 18
ggactgccgg caaatgcctc cacagtggtc ggaggagacg tagagtttgt ctgcaaggtt       60
tacagtgatg cccagcccca catccagtgg atcaagcacg tggaaaagaa cggcagtaaa      120
tacgggcccg acgggctgcc ctacctcaag gttctcaagg tgaggacttt ctgaatctaa      180
agg                                                                    183

<210> SEQ ID NO 19
<211> LENGTH: 178
```

```
<212> TYPE: DNA
<213> ORGANISM: Artificial Sequence
<220> FEATURE:
<223> OTHER INFORMATION: Synthetic oligonucleotide

<400> SEQUENCE: 19
cctcaaggtt ctcaaggtga ggactttctg aatctaaagg tacccacaac tggggtctcc      60
ttcatgggtt tggccacagg ttctttgatt tcctgttgga gttgagagag gatgattctc     120 tttttttgact agccagcaga gagtgttcta aggggatcga cgagagcagc gcgactgg      178

<210> SEQ ID NO 20
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 20
cgacactgct cgatccgctc gcacctttct ggcatgaggt cactgacagc cctctgg        57

<210> SEQ ID NO 21
<211> LENGTH: 121
<212> TYPE: DNA
<213> ORGANISM: Artificial Sequence
<220> FEATURE:
<223> OTHER INFORMATION: Synthetic oligonucleotide

<400> SEQUENCE: 21
ggcatgaggt cactgacagc cctctggaca acacagctta tttattggtc tctcattctc      60
ccatccccac tcctcctttc ttccctctct ccaccagagc gatggcgtca ccggcccatc     120
c                                                                     121

<210> SEQ ID NO 22
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 22
cgatggcgtc accggcccat cctccaagcc ggactgccgg caaatgcctc cacagtggtc      60
ggaggagacg tagagtttgt ctgcaaggtt tacagtgatg                            100

<210> SEQ ID NO 23
<211> LENGTH: 112
<212> TYPE: DNA
<213> ORGANISM: Artificial Sequence
<220> FEATURE:
<223> OTHER INFORMATION: Synthetic oligonucleotide

<400> SEQUENCE: 23
ggagacgtag agtttgtctg caaggtttac agtgatgccc agcccacat ccagtggatc       60 aagcacgtgg aaaagaacgg cagtaaatac gggcccgacg ggctgcccta cc             112

<210> SEQ ID NO 24
<211> LENGTH: 119
<212> TYPE: DNA
<213> ORGANISM: Artificial Sequence
<220> FEATURE:
<223> OTHER INFORMATION: Synthetic oligonucleotide

<400> SEQUENCE: 24
```

```
gcccgacggg ctgccctacc tcaaggttct caaggtgagg actttctgaa tctaaaggta    60
cccacaactg gggtctcctt catgggtttg gccacaggtt ctttgattte ctgttggag    119

<210> SEQ ID NO 25
<211> LENGTH: 112
<212> TYPE: DNA
<213> ORGANISM: Artificial Sequence
<220> FEATURE:
<223> OTHER INFORMATION: Synthetic oligonucleotide

<400> SEQUENCE: 25
ggtttggcca caggttcttt gatttcctgt tggagttgag agaggatgat tctcttttt    60 gactagccag cagagagtgt tctaagggga tcgacgagag cagcgcgact gg           112

<210> SEQ ID NO 26
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 26
cgacactgct cgatccgctc gcacctttct ggcatgaggt cactgacagc cctctggaca    60
acacagctta tttattggtc tctcattctc ccatccccac                         100

<210> SEQ ID NO 27
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 27
cctctggaca acacagctta tttattggtc tctcattctc ccatccccac tcctcctttc    60
ttccctctct ccaccagagc gatggcgtca ccggcccatc                         100

<210> SEQ ID NO 28
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 28
tcctcctttc ttccctctct ccaccagagc gatggcgtca ccggcccatc ctccaagccg    60
gactgccggc aaatgcctcc acagtggtcg gaggagacgt                         100

<210> SEQ ID NO 29
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 29
ctccaagccg gactgccggc aaatgcctcc acagtggtcg gaggagacgt agagtttgtc    60
tgcaaggttt acagtgatgc ccagccccac atccagtgga                         100

<210> SEQ ID NO 30
<211> LENGTH: 100
<212> TYPE: DNA
<213> ORGANISM: Artificial Sequence
```

<220> FEATURE:
<223> OTHER INFORMATION: Synthetic oligonucleotide

<400> SEQUENCE: 30
agagtttgtc tgcaaggttt acagtgatgc ccagccccac atccagtgga tcaagcacgt    60
ggaaaagaac ggcagtaaat acgggcccga cgggctgccc                         100

<210> SEQ ID NO 31
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 31
tcaagcacgt ggaaaagaac ggcagtaaat acgggcccga cgggctgccc tacctcaagg    60
ttctcaaggt gaggactttc tgaatctaaa ggtacccaca                         100

<210> SEQ ID NO 32
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 32
tacctcaagg ttctcaaggt gaggactttc tgaatctaaa ggtacccaca actggggtct    60
ccttcatggg tttggccaca ggttctttga tttcctgttg                         100

<210> SEQ ID NO 33
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 33
actggggtct ccttcatggg tttggccaca ggttctttga tttcctgttg gagttgagag    60
aggatgattc tcttttttga ctagccagca gagagtgttc                         100

<210> SEQ ID NO 34
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 34
gagttgagag aggatgattc tcttttttga ctagccagca gagagtgttc taagggggatc   60 gacgagagca gcgcgactgg                                                80

<210> SEQ ID NO 35
<211> LENGTH: 140
<212> TYPE: DNA
<213> ORGANISM: Artificial Sequence
<220> FEATURE:
<223> OTHER INFORMATION: Synthetic oligonucleotide

<400> SEQUENCE: 35
cgacactgct cgatccgctc gcaccgcacc tgtacgatca ctgaactgca gaatctggga    60
tgttaaccag aagaccttct atctgaggaa caaccaacta gttgctggat acttgcaagg   120

```
accaaatgtc aatttagaag                                                  140

<210> SEQ ID NO 36
<211> LENGTH: 183
<212> TYPE: DNA
<213> ORGANISM: Artificial Sequence
<220> FEATURE:
<223> OTHER INFORMATION: Synthetic oligonucleotide

<400> SEQUENCE: 36
gttgctggat acttgcaagg accaaatgtc aatttagaag aaaagttcga catgtccttt      60
gtagaaggac atgaaagtaa tgacaaaata cctgtggcct tgggcctcaa ggaaaagaat    120
ctgtacctgt cctgcgtgtt gaaagatgat gaacccactc tacagctgga ggctgtaaat    180
ccc                                                                   183

<210> SEQ ID NO 37
<211> LENGTH: 157
<212> TYPE: DNA
<213> ORGANISM: Artificial Sequence
<220> FEATURE:
<223> OTHER INFORMATION: Synthetic oligonucleotide

<400> SEQUENCE: 37
gaacccactc tacagctgga ggctgtaaat cccaaaaatt acccaaagag gaagatggaa      60
aagcgatttg tcttcaacaa gatagattca ggcccaacca catcatttga gtctgcccag    120
ttccccaact ggttcctctg cacagcgatg gaagctg                              157

<210> SEQ ID NO 38
<211> LENGTH: 131
<212> TYPE: DNA
<213> ORGANISM: Artificial Sequence
<220> FEATURE:
<223> OTHER INFORMATION: Synthetic oligonucleotide

<400> SEQUENCE: 38
ctggttcctc tgcacagcga tggaagctga ccagcccgtc agcctcacca atatgcctga      60
cgaaggcgtc atggtcacca aattctacat gcaatttgtg tcttccggat cgacgagagc    120
agcgcgactg g                                                          131

<210> SEQ ID NO 39
<211> LENGTH: 73
<212> TYPE: DNA
<213> ORGANISM: Artificial Sequence
<220> FEATURE:
<223> OTHER INFORMATION: Synthetic oligonucleotide

<400> SEQUENCE: 39
cgacactgct cgatccgctc gcaccgcacc tgtacgatca ctgaactgca gaatctggga      60
tgttaaccag aag                                                         73

<210> SEQ ID NO 40
<211> LENGTH: 123
<212> TYPE: DNA
<213> ORGANISM: Artificial Sequence
<220> FEATURE:
<223> OTHER INFORMATION: Synthetic oligonucleotide

<400> SEQUENCE: 40
cgatcactga actgcagaat ctgggatgtt aaccagaaga ccttctatct gaggaacaac      60
caactagttg ctggatactt gcaaggacca aatgtcaatt tagaagaaaa gttcgacatg    120
```

| tcc | 123 |

<210> SEQ ID NO 41
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 41

| atgtcaattt agaagaaaag ttcgacatgt cctttgtaga aggacatgaa agtaatgaca | 60 |
| aaatacctgt ggccttgggc ctcaagg | 87 |

<210> SEQ ID NO 42
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 42

| acctgtggcc ttgggcctca aggaaaagaa tctgtacctg tcctgcgtgt tgaaagatga | 60 |
| tgaacccact ctacagctgg aggctgtaaa tccc | 94 |

<210> SEQ ID NO 43
<211> LENGTH: 125
<212> TYPE: DNA
<213> ORGANISM: Artificial Sequence
<220> FEATURE:
<223> OTHER INFORMATION: Synthetic oligonucleotide

<400> SEQUENCE: 43

| gaacccactc tacagctgga ggctgtaaat cccaaaaatt acccaaagag gaagatggaa | 60 |
| aagcgatttg tcttcaacaa gatagattca ggcccaacca catcatttga gtctgcccag | 120 |
| ttccc | 125 |

<210> SEQ ID NO 44
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 44

| aaccacatca tttgagtctg cccagttccc caactggttc ctctgcacag cgatggaagc | 60 |
| tgaccagccc gtcagcctca ccaatatgcc tgacgaaggc | 100 |

<210> SEQ ID NO 45
<211> LENGTH: 94
<212> TYPE: DNA
<213> ORGANISM: Artificial Sequence
<220> FEATURE:
<223> OTHER INFORMATION: Synthetic oligonucleotide

<400> SEQUENCE: 45

| gtcagcctca ccaatatgcc tgacgaaggc gtcatggtca ccaaattcta catgcaattt | 60 |
| gtgtcttccg gatcgacgag agcagcgcga ctgg | 94 |

<210> SEQ ID NO 46
<211> LENGTH: 100
<212> TYPE: DNA

<213> ORGANISM: Artificial Sequence
<220> FEATURE:
<223> OTHER INFORMATION: Synthetic oligonucleotide

<400> SEQUENCE: 46
cgacactgct cgatccgctc gcaccgcacc tgtacgatca ctgaactgca gaatctggga    60
tgttaaccag aagaccttct atctgaggaa caaccaacta                         100

<210> SEQ ID NO 47
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 47
gaatctggga tgttaaccag aagaccttct atctgaggaa caaccaacta gttgctggat    60
acttgcaagg accaaatgtc aatttagaag aaaagttcga                         100

<210> SEQ ID NO 48
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 48
agttgctgga tacttgcaag gaccaaatgt caatttagaa gaaaagttcg acatgtcctt    60
tgtagaagga catgaaagta atgacaaaat acctgtggcc                         100

<210> SEQ ID NO 49
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 49
acatgtcctt tgtagaagga catgaaagta atgacaaaat acctgtggcc ttgggcctca    60
aggaaaagaa tctgtacctg tcctgcgtgt tgaaagatga                         100

<210> SEQ ID NO 50
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 50
cttgggcctc aaggaaaaga atctgtacct gtcctgcgtg ttgaaagatg atgaacccac    60
tctacagctg gaggctgtaa atcccaaaaa ttacccaaag                         100

<210> SEQ ID NO 51
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 51
atgaacccac tctacagctg gaggctgtaa atcccaaaaa ttacccaaag aggaagatgg    60
aaaagcgatt tgtcttcaac aagatagatt caggcccaac                         100

<210> SEQ ID NO 52
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 52
gaggaagatg gaaaagcgat ttgtcttcaa caagatagat tcaggcccaa ccacatcatt    60
tgagtctgcc cagttcccca actggttcct ctgcacagcg                         100

<210> SEQ ID NO 53
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 53
ccacatcatt tgagtctgcc cagttcccca actggttcct ctgcacagcg atggaagctg    60
accagcccgt cagcctcacc aatatgcctg acgaaggcgt                         100

<210> SEQ ID NO 54
<211> LENGTH: 113
<212> TYPE: DNA
<213> ORGANISM: Artificial Sequence
<220> FEATURE:
<223> OTHER INFORMATION: Synthetic oligonucleotide

<400> SEQUENCE: 54
gatggaagct gaccagcccg tcagcctcac caatatgcct gacgaaggcg tcatggtcac    60
caaattctac atgcaatttg tgtcttccgg atcgacgaga gcagcgcgac tgg          113

<210> SEQ ID NO 55
<211> LENGTH: 135
<212> TYPE: DNA
<213> ORGANISM: Artificial Sequence
<220> FEATURE:
<223> OTHER INFORMATION: Synthetic oligonucleotide

<400> SEQUENCE: 55
cgacactgct cgatccgctc gcacccatat ggccaagctg accagcgccg ttccggtgct    60
caccgcgcgc gacgtcgccg gagcggtcga gttctggacc gaccggctcg ggttctcccg   120
ggacttcgtg gagga                                                    135

<210> SEQ ID NO 56
<211> LENGTH: 164
<212> TYPE: DNA
<213> ORGANISM: Artificial Sequence
<220> FEATURE:
<223> OTHER INFORMATION: Synthetic oligonucleotide

<400> SEQUENCE: 56
gggttctccc gggacttcgt ggaggacgac ttcgccggtg tggtccggga cgacgtgacc    60
ctgttcatca gcgcggtcca ggaccaggta agacgcaatt ctgctgtgca cgtgccaatg   120
ccgctgcccc ccagcgcatt ggctcaccat cgccatcgcc attg                    164

<210> SEQ ID NO 57
<211> LENGTH: 115
<212> TYPE: DNA

<213> ORGANISM: Artificial Sequence
<220> FEATURE:
<223> OTHER INFORMATION: Synthetic oligonucleotide

<400> SEQUENCE: 57
cattggctca ccatcgccat cgccattgct gctgcaggtg gtgccggaca acaccctggc    60
ctgggtgtgg gtgcgcggcc tggacgagct gtacgccgag tggtcggagg tcgtg        115

<210> SEQ ID NO 58
<211> LENGTH: 185
<212> TYPE: DNA
<213> ORGANISM: Artificial Sequence
<220> FEATURE:
<223> OTHER INFORMATION: Synthetic oligonucleotide

<400> SEQUENCE: 58
gtacgccgag tggtcggagg tcgtgtccac gaacttccgg gacgcctccg ggccggccat    60
gaccgagatc ggcgagcagc cgtggggcg ggagttcgcc ctgcgcgacc cggccggcaa    120
ctgcgtgcac ttcgtggccg aggagcagga ctaaggatcc ggatcgacga gagcagcgcg    180
actgg                                                                185

<210> SEQ ID NO 59
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 59
cgacactgct cgatccgctc gcacccatat ggccaagctg accagcgccg ttcc          54

<210> SEQ ID NO 60
<211> LENGTH: 121
<212> TYPE: DNA
<213> ORGANISM: Artificial Sequence
<220> FEATURE:
<223> OTHER INFORMATION: Synthetic oligonucleotide

<400> SEQUENCE: 60
gccaagctga ccagcgccgt tccggtgctc accgcgcgcg acgtcgccgg agcggtcgag    60
ttctggaccg accggctcgg gttctcccgg gacttcgtgg aggacgactt cgccggtgtg    120
g                                                                    121

<210> SEQ ID NO 61
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 61
tggaggacga cttcgccggt gtggtccggg acgacgtgac cctgttcatc agcgcggtcc    60
aggaccaggt aagacgcaat tctgctg                                        87

<210> SEQ ID NO 62
<211> LENGTH: 92
<212> TYPE: DNA
<213> ORGANISM: Artificial Sequence
<220> FEATURE:
<223> OTHER INFORMATION: Synthetic oligonucleotide

<400> SEQUENCE: 62

```
gtccaggacc aggtaagacg caattctgct gtgcacgtgc caatgccgct gcccccccagc    60 gcattggctc accatcgcca tcgccattgc tg                                   92

<210> SEQ ID NO 63
<211> LENGTH: 104
<212> TYPE: DNA
<213> ORGANISM: Artificial Sequence
<220> FEATURE:
<223> OTHER INFORMATION: Synthetic oligonucleotide

<400> SEQUENCE: 63
caccatcgcc atcgccattg ctgctgcagg tggtgccgga caacaccctg gcctgggtgt    60
gggtgcgcgg cctggacgag ctgtacgccg agtggtcgga ggtc                    104

<210> SEQ ID NO 64
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 64
gctgtacgcc gagtggtcgg aggtcgtgtc cacgaacttc cgggacgcct ccgggccggc    60
catgaccgag atcggcgagc agcc                                            84

<210> SEQ ID NO 65
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 65
ccatgaccga gatcggcgag cagccgtggg ggcgggagtt cgccctgcgc gacccggccg    60
gcaactgcgt gcacttcgtg gccgaggagc aggactaagg                         100

<210> SEQ ID NO 66
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 66
cacttcgtgg ccgaggagca ggactaagga tccggatcga cgagagcagc gcgactgg      58

<210> SEQ ID NO 67
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 67
cgacactgct cgatccgctc gcacccatat ggccaagctg accagcgccg ttccggtgct    60
caccgcgcgc gacgtcgccg gagcggtcga gttctggacc                         100

<210> SEQ ID NO 68
<211> LENGTH: 100
<212> TYPE: DNA
<213> ORGANISM: Artificial Sequence
<220> FEATURE:
```

<223> OTHER INFORMATION: Synthetic oligonucleotide

<400> SEQUENCE: 68
ttccggtgct caccgcgcgc gacgtcgccg gagcggtcga gttctggacc gaccggctcg    60
ggttctcccg ggacttcgtg gaggacgact cgccggtgt                          100

<210> SEQ ID NO 69
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 69
cgaccggctc gggttctccc gggacttcgt ggaggacgac ttcgccggtg tggtccggga    60
cgacgtgacc ctgttcatca gcgcggtcca ggaccaggta                         100

<210> SEQ ID NO 70
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 70
tggtccggga cgacgtgacc ctgttcatca gcgcggtcca ggaccaggta agacgcaatt    60
ctgctgtgca cgtgccaatg ccgctgcccc ccagcgcatt                         100

<210> SEQ ID NO 71
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 71
aagacgcaat tctgctgtgc acgtgccaat gccgctgccc ccagcgcat tggctcacca    60 tcgccatcgc cattgctgct gcaggtggtg ccggacaaca                         100

<210> SEQ ID NO 72
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 72
tggctcacca tcgccatcgc cattgctgct gcaggtggtg ccggacaaca ccctggcctg    60
ggtgtgggtg cgcggcctgg acgagctgta cgccgagtgg                         100

<210> SEQ ID NO 73
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 73
accctggcct gggtgtgggt gcgcggcctg gacgagctgt acgccgagtg gtcggaggtc    60
gtgtccacga acttccggga cgcctccggg ccggccatga                         100

```
<210> SEQ ID NO 74
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 74
gtcggaggtc gtgtccacga acttccggga cgcctccggg ccggccatga ccgagatcgg    60
cgagcagccg tgggggcggg agttcgccct gcgcgacccg                         100

<210> SEQ ID NO 75
<211> LENGTH: 124
<212> TYPE: DNA
<213> ORGANISM: Artificial Sequence
<220> FEATURE:
<223> OTHER INFORMATION: Synthetic oligonucleotide

<400> SEQUENCE: 75
accgagatcg gcgagcagcc gtgggggcgg gagttcgccc tgcgcgaccc ggccggcaac    60
tgcgtgcact cgtggccga ggagcaggac taaggatccg gatcgacgag agcagcgcga   120
ctgg                                                               124

<210> SEQ ID NO 76
<211> LENGTH: 392
<212> TYPE: DNA
<213> ORGANISM: Artificial Sequence
<220> FEATURE:
<223> OTHER INFORMATION: Synthetic oligonucleotide

<400> SEQUENCE: 76
accggttcct gggcccagtc tgccctgact cagcctgcct ccgtgtctgg gtctcctgga    60
cagtcgatca ccatctcctg caatggaacc agcagtgacg ttggtggatt tgactctgtc   120
tcctggtacc aacagcaccc aggcaaagcc cccaaactca tgatttatga tgtcagtcat   180
cggccctcag gggtttctaa tcgcttctct ggctccaagt ctggcaacac ggcctccctg   240
accatctctg gctccaggc tgaggacgag gctgattatt actgctcttc actgacagac   300
agaagccatc gcatattcgg cggagggacc aagctgaccg tcctaggtca gcccaaggct   360
gccccctcgg tcactctgtt cccgccctcg ag                                392

<210> SEQ ID NO 77
<211> LENGTH: 173
<212> TYPE: DNA
<213> ORGANISM: Artificial Sequence
<220> FEATURE:
<223> OTHER INFORMATION: Synthetic oligonucleotide

<400> SEQUENCE: 77
cgacactgct cgatccgctc gcaccaccgg ttcctgggcc cagtctgccc tgactcagcc    60
tgcctccgtg tctgggtctc ctggacagtc gatcaccatc tcctgcaatg gaaccagcag   120
tgacgttggt ggatttgact ctgtctcctg gtaccaacag cacccaggca aag          173

<210> SEQ ID NO 78
<211> LENGTH: 151
<212> TYPE: DNA
<213> ORGANISM: Artificial Sequence
<220> FEATURE:
<223> OTHER INFORMATION: Synthetic oligonucleotide

<400> SEQUENCE: 78
```

```
ctcctggtac aacagcacc caggcaaagc ccccaaactc atgatttatg atgtcagtca    60
tcggccctca ggggtttcta atcgcttctc tggctccaag tctggcaaca cggcctccct   120
gaccatctct gggctccagg ctgaggacga g                                  151
```

<210> SEQ ID NO 79
<211> LENGTH: 172
<212> TYPE: DNA
<213> ORGANISM: Artificial Sequence
<220> FEATURE:
<223> OTHER INFORMATION: Synthetic oligonucleotide

<400> SEQUENCE: 79

```
ctctgggctc caggctgagg acgaggctga ttattactgc tcttcactga cagacagaag    60
ccatcgcata ttcggcggag ggaccaagct gaccgtccta ggtcagccca aggctgcccc   120
ctcggtcact ctgttcccgc cctcgaggga tcgacgagag cagcgcgact gg           172
```

<210> SEQ ID NO 80
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 80

```
accggttcct gggcc                                                     15
```

<210> SEQ ID NO 81
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 81

```
ctcgagggcg ggaacag                                                   17
```

<210> SEQ ID NO 82
<211> LENGTH: 1308
<212> TYPE: DNA
<213> ORGANISM: Artificial Sequence
<220> FEATURE:
<223> OTHER INFORMATION: Synthetic oligonucleotide

<400> SEQUENCE: 82

```
cgacactgct cgatccgctc gcaccccgcc ttgtttaact ttaagaagga gcccttcccc    60
atgacaagaa caagtttgcc ttttccagac ggtttcctgt ggggcgcaag cacggcggct   120
caccagattg aaggtaataa tgtaaatagt gattggtgga aaaagaaca tgaccctgct    180 gcaaatattg cagaaccatc tttggatgcc tgtgactcat atcaccgctg ggaacaagat   240
atggacctgt tagcagaact gggctttacc gattaccgct tctccgttga atgggcccgt   300
attgaacctg tgccaggtac attttcgcat gctgaaacgg cacactatcg tagaatggtt   360
gatggtgctt tggcaagagg cctgcgccca atggtcaccc tgcatcactt tactgtaccg   420
cagtggttcg aagatttggg tggctggaca gccgatggtg ccgcgacct gtttgcacgt   480 tacgtcgaac attgtgctcc gattatcggt aaagatgtta gacacgtgtg cacgattaat   540
gaacctaaca tgatcgccgt aatggcgggc ttagctaaga caggcgatca aggtttccca   600
ccggcgggtt tgcctacgcc tgacgaagaa accactcatg ctgttattgc tgcacatcac    660
gccgcggtca aagcagtacg tgccattgat ccggacatcc aggtcggctg gaccatcgct   720
```

| | |
|---|---|
| aatcaagtat atcaggcatt acctggtgcc gaagatgtta ctgctgcata tcgttaccca | 780 |
| agagaagacg tgttcattga agccgctcgt ggcgatgact ggatcggcgt gcaatcttac | 840 |
| acacgcacga agattggtgc ggatggccca atcccggcgc ctgaagacgc tgaacgcacc | 900 |
| ctgactcagt gggaatatta cccagctgct gttggtcatg ctctgcgtca cacagcggat | 960 |
| gtcgctggcc cagacatgcc gttaattgta accgaaaacg gtatcgccac tgcggatgac | 1020 |
| gcacgccgtg tggattatta cactggtgca ctggaagccg tttcagccgc gttagaagat | 1080 |
| ggtgtgaata ttcatggcta tctggcgtgg agcgctttgg ataactatga atggggtagt | 1140 |
| tacaaaccga cttttggcct gatccgcagtt gatcctgtga cattcgaaag aacggccaag | 1200 |
| ccgtcagcag tgtggttagg tgaaatgggt agaacaagac agttgccaag agcggaacgc | 1260 |
| gggaagggtg ggcgcgccga cccggatcga cgagagcagc gcgactgg | 1308 |

<210> SEQ ID NO 83
<211> LENGTH: 161
<212> TYPE: DNA
<213> ORGANISM: Artificial Sequence
<220> FEATURE:
<223> OTHER INFORMATION: Synthetic oligonucleotide

<400> SEQUENCE: 83

| | |
|---|---|
| cgacactgct cgatccgctc gcaccccgcc ttgtttaact ttaagaagga gcccttcccc | 60 |
| atgacaagaa caagtttgcc ttttccagac ggtttcctgt ggggcgcaag cacggcggct | 120 |
| caccagattg aaggtaataa tgtaaatagt gattggtgga g | 161 |

<210> SEQ ID NO 84
<211> LENGTH: 172
<212> TYPE: DNA
<213> ORGANISM: Artificial Sequence
<220> FEATURE:
<223> OTHER INFORMATION: Synthetic oligonucleotide

<400> SEQUENCE: 84

| | |
|---|---|
| gctcaccaga ttgaaggtaa taatgtaaat agtgattggt ggagaaaaga acatgaccct | 60 |
| gctgcaaata ttgcagaacc atctttggat gcctgtgact catatcaccg ctgggaacaa | 120 |
| gatatggacc tgttagcaga actgggcttt accgattacc gcttctccgt tg | 172 |

<210> SEQ ID NO 85
<211> LENGTH: 138
<212> TYPE: DNA
<213> ORGANISM: Artificial Sequence
<220> FEATURE:
<223> OTHER INFORMATION: Synthetic oligonucleotide

<400> SEQUENCE: 85

| | |
|---|---|
| gaactgggct ttaccgatta ccgcttctcc gttgaatggg cccgtattga acctgtgcca | 60 |
| ggtacatttt cgcatgctga aacggcacac tatcgtagaa tggttgatgg tgctttggca | 120 |
| agaggcctgc gcccaatg | 138 |

<210> SEQ ID NO 86
<211> LENGTH: 158
<212> TYPE: DNA
<213> ORGANISM: Artificial Sequence
<220> FEATURE:
<223> OTHER INFORMATION: Synthetic oligonucleotide

<400> SEQUENCE: 86

```
ctttggcaag aggcctgcgc ccaatggtca ccctgcatca ctttactgta ccgcagtggt    60
tcgaagattt gggtggctgg acagccgatg gtgccgcgga cctgtttgca cgttacgtcg    120
aacattgtgc tccgattatc ggtaaagatg ttagacac                            158
```

<210> SEQ ID NO 87
<211> LENGTH: 152
<212> TYPE: DNA
<213> ORGANISM: Artificial Sequence
<220> FEATURE:
<223> OTHER INFORMATION: Synthetic oligonucleotide

<400> SEQUENCE: 87

```
gtcgaacatt gtgctccgat tatcggtaaa gatgttagac acgtgtgcac gattaatgaa    60
cctaacatga tcgccgtaat ggcgggctta gctaagacag gcgatcaagg tttcccaccg    120
gcgggtttgc ctacgcctga cgaagaaacc ac                                  152
```

<210> SEQ ID NO 88
<211> LENGTH: 158
<212> TYPE: DNA
<213> ORGANISM: Artificial Sequence
<220> FEATURE:
<223> OTHER INFORMATION: Synthetic oligonucleotide

<400> SEQUENCE: 88

```
gggtttgcct acgcctgacg aagaaaccac tcatgctgtt attgctgcac atcacgccgc    60
ggtcaaagca gtacgtgcca ttgatccgga catccaggtc ggctggacca tcgctaatca    120
agtatatcag gcattacctg gtgccgaaga tgttactg                            158
```

<210> SEQ ID NO 89
<211> LENGTH: 193
<212> TYPE: DNA
<213> ORGANISM: Artificial Sequence
<220> FEATURE:
<223> OTHER INFORMATION: Synthetic oligonucleotide

<400> SEQUENCE: 89

```
atcaggcatt acctggtgcc gaagatgtta ctgctgcata tcgttaccca agagaagacg    60
tgttcattga agccgctcgt ggcgatgact ggatcggcgt gcaatcttac acacgcacga    120
agattggtgc ggatggccca atcccggcgc tgaagacgc tgaacgcacc ctgactcagt    180
gggaatatta ccc                                                       193
```

<210> SEQ ID NO 90
<211> LENGTH: 185
<212> TYPE: DNA
<213> ORGANISM: Artificial Sequence
<220> FEATURE:
<223> OTHER INFORMATION: Synthetic oligonucleotide

<400> SEQUENCE: 90

```
ctgaacgcac cctgactcag tgggaatatt acccagctgc tgttggtcat gctctgcgtc    60
acacagcgga tgtcgctggc ccagacatgc cgttaattgt aaccgaaaac ggtatcgcca    120
ctgcggatga cgcacgccgt gtggattatt acactggtgc actggaagcc gtttcagccg    180
cgtta                                                                185
```

<210> SEQ ID NO 91
<211> LENGTH: 153
<212> TYPE: DNA
<213> ORGANISM: Artificial Sequence -continued

```
<220> FEATURE:
<223> OTHER INFORMATION: Synthetic oligonucleotide

<400> SEQUENCE: 91
gcactggaag ccgtttcagc cgcgttagaa gatggtgtga atattcatgg ctatctggcg      60
tggagcgctt tggataacta tgaatggggt agttacaaac cgacttttgg cctgatcgca     120
gttgatcctg tgacattcga aagaacggcc aag                                  153

<210> SEQ ID NO 92
<211> LENGTH: 143
<212> TYPE: DNA
<213> ORGANISM: Artificial Sequence
<220> FEATURE:
<223> OTHER INFORMATION: Synthetic oligonucleotide

<400> SEQUENCE: 92
cagttgatcc tgtgacattc gaaagaacgg ccaagccgtc agcagtgtgg ttaggtgaaa      60
tgggtagaac aagacagttg ccaagagcgg aacgcgggaa gggtgggcgc gccgacccgg     120
atcgacgaga gcagcgcgac tgg                                             143
```

SYNTHESIS OF LONG NUCLEIC ACID SEQUENCES

CROSS-REFERENCE TO RELATED APPLICATIONS

This patent application is a continuation of U.S. Nonprovisional patent application Ser. No. 14/865,127 filed Sep. 25, 2015, which claims priority to U.S. Nonprovisional patent application Ser. No. 13/742,959 filed Jan. 16, 2013 which claims priority to U.S. Provisional Patent Application No. 61/587,073 filed Jan. 16, 2012, the content of which is incorporated herein by reference in its entirety.

SEQUENCE LISTING

The sequence listing is filed with the application in electronic format only and is incorporated by reference herein. The sequence listing text file "Gene Assembly PA2013-01 Sequence Listing" was created on Jan. 16, 2013 and is 34,660 bytes in size.

FIELD OF THE INVENTION

This invention pertains to the synthesis of genes or gene fragments.

BACKGROUND OF THE INVENTION

Synthetic DNA sequences are a vital tool in molecular biology. They are used in gene therapy, vaccines, DNA libraries, environmental engineering, diagnostics, tissue engineering and research into genetic variants. Long artificially-made nucleic acid sequences are commonly referred to as synthetic genes; however the synthesized artificial elements do not have to encode genes, but, for example, can be regulatory or structural elements. Regardless of functional usage, long artificially-assembled nucleic acids will be referred to herein as synthetic genes and the process of manufacturing these species will be referred to as gene synthesis. Gene synthesis provides an advantageous alternative from obtaining genetic elements through traditional means, such as isolation from a genomic DNA library, isolation from a cDNA library, or PCR cloning. Traditional cloning requires availability of a suitable library constructed from isolated natural nucleic acids wherein the abundance of the gene element of interest is at a level that assures a successful isolation and recovery. Further, a gene isolated from genomic DNA or cDNA libraries only provides an isolate having that nucleic acid sequence as it exists in nature. It is often desirable to introduce alterations into that sequence. For example, gene synthesis allows for complete revision of codon usage, which may be necessary to achieve efficient synthesis and expression of a human gene product in a bacterial vector. As another example, a synthetic gene can have restriction sites removed and new sites added. As yet another example, a synthetic gene can have novel regulatory elements or processing signals included which are not present in the native gene. Many other examples of the utility of gene synthesis are well known to those with skill in the art.

Artificial gene synthesis can also provide a DNA sequence that is codon optimized. Given codon redundancy, many different DNA sequences can encode the same amino acid sequence. Codon preferences differ between organisms and a gene sequence that is expressed well in one organism might be expressed poorly or not at all when introduced into a different organism. The efficiency of expression can be adjusted by changing the nucleotide sequence so that the element is well expressed in whatever organism is desired, e.g., it is adjusted for the codon bias of that organism. Widespread changes of this kind are easily made using gene synthesis methods but are not feasible using site-directed mutagenesis or other methods which introduce alterations into naturally isolated nucleic acids.

Gene synthesis employs synthetic oligonucleotides as the primary building block. Oligonucleotides are typically made using chemical synthesis, most commonly using betacyanoethyl phosphoramidite methods, which are well-known to those with skill in the art (M. H. Caruthers, Methods in Enzymology 154, 287-313 (1987)). Using a four-step process, phosphoramidite monomers are added in a 3' to 5' direction to form an oligonucleotide chain. During each cycle of monomer addition, a small amount of oligonucleotides will fail to couple (n−1 product). Therefore, with each subsequent monomer addition the cumulative population of failures grows. Also, as the oligonucleotide grows longer, the base addition chemistry becomes less efficient, presumably due to steric issues with chain folding. Typically, oligonucleotide synthesis proceeds with a base coupling efficiency of around 99.0 to 99.2%. A 20 base long oligonucleotide requires 19 base coupling steps. Thus assuming a 99% coupling efficiency, a 20 base oligonucleotide should have $0.99^{19}$ purity, meaning approximately 82% of the final end product will be full length and 18% will be truncated failure products. A 40 base oligonucleotide should have $0.99^{39}$ purity, meaning approximately 68% of the final end product will be full length and 32% will be truncated failure products. A 100 base oligonucleotide should have $0.99^{99}$ purity, meaning approximately 37% of the final product will be full length and 63% will be truncated failure products. In contrast, if the efficiency of base coupling is increased to 99.5%, then a 100 base oligonucleotide should have a $0.995^{99}$ purity, meaning approximately 61% of the final product will be full length and 39% will be truncated failure products.

Using gene synthesis methods, a series of synthetic oligonucleotides are assembled into a longer synthetic nucleic acid, e.g. a synthetic gene. The use of synthetic oligonucleotide building blocks in gene synthesis methods with a high percentage of failure products present will decrease the quality of the final product, requiring implementation of costly and time-consuming error correction methods. For this reason, relatively short synthetic oligonucleotides in the 40-60 base length range have typically been employed in gene synthesis methods, even though longer oligonucleotides could have significant benefits in assembly. It is well appreciated by those with skill in the art that use of high quality synthetic oligonucleotides, e.g. oligonucleotides with few error or missing bases, will result in high quality assembly of synthetic genes that use of lower quality synthetic oligonucleotides.

Some common forms of gene assembly are ligation-based assembly, PCR-driven assembly (see Tian et al., Mol. BioSyst., 5, 714-722 (2009)) and thermodynamically balanced inside-out based PCR (TBIO) (see Gao X. et al., *Nucleic Acids Res.* 31, e143). All three methods combine multiple shorter oligonucleotides into a single longer end-product.

Therefore, to make genes that are typically 500 to many thousands of bases long, a large number of smaller oligonucleotides are synthesized and combined through ligation, overlapping, etc., after synthesis. Typically, gene synthesis methods only function well when combining a limited number of synthetic oligonucleotide building blocks and very large genes must be constructed from smaller subunits using iterative methods. For example, 10-20 of 40-60 base overlapping oligonucleotides are assembled into a single 500 base subunit due to the need for overlapping ends, and twelve or more 500 base overlapping subunits are assembled into a single 5000 base synthetic gene. Each subunit of this process is typically cloned (i.e., ligated into a plasmid vector, transformed into a bacterium, expanded, and purified) and its DNA sequence is verified before proceeding to the next step. If the above gene synthesis process has low fidelity, either due to errors introduced by low quality of the initial oligonucleotide building blocks or during the enzymatic steps of subunit assembly, then increasing numbers of cloned isolates must be sequence verified to find a perfect clone to move forward in the process or an error-containing clone must have the error corrected using site directed mutagenesis. Regardless, sequence errors increase cost and increase time of the manufacturing process. Any improvement in quality of the input oligonucleotides or assembly method that increases fidelity of the final product is desirable.

The methods of the invention described herein provide high quality oligonucleotide subunits that are ideal for gene synthesis and improved methods to assemble said subunits into longer genetic elements. These and other advantages of the invention, as well as additional inventive features, will be apparent from the description of the invention provided herein.

BRIEF SUMMARY OF THE INVENTION

The methods include the manufacture of long double-stranded nucleic acid elements that can optionally be inserted into a variety of vectors and clonally amplified.

In one embodiment, synthetic nucleic acid elements are diluted, typically to 0.25 to 10 copies per reaction well, amplified and sequence verified, resulting in a large amount of homogeneous, desired product (a "gene block"). In a further embodiment, the synthetic nucleic acid elements are diluted to 1-5 copies of the synthesized oligonucleotide per reaction well, and in a further embodiment the synthetic nucleic acid elements are diluted to 2-4 copies per reaction well. In a further embodiment, the synthetics nucleic acid elements are greater than 60 bases. In a further embodiment, the synthetics nucleic acid elements are greater than 100 bases.

In a further embodiment, the gene block is comprised of two or more smaller synthetic nucleic acid elements ("gene sub-blocks") that are bound or covalently linked together to form the gene block, which is then diluted. The gene block can be joined with one or more additional gene blocks to make longer fragments in an iterative fashion.

The gene blocks can then be inserted into vectors, such as bacterial DNA plasmids, and clonally amplified through methods well-known in the art.

In a further embodiment, gene blocks are synthesized or combined in such a manner as to provide 3' and 5' flanking sequences that enable the synthetic nucleic acid elements to be more easily inserted into a vector for isothermal amplification.

In another embodiment, the component oligonucleotide(s) that are employed to synthesize the synthetic nucleic acid elements are high-fidelity (i.e., low error) oligonucleotides synthesized on supports comprised of thermoplastic polymer and controlled pore glass (CPG), wherein the amount of CPG per support by percentage is between 1-8% by weight.

In another embodiment, a set of oligonucleotides are joined or combined through top-strand PCR amplification (TSP), wherein a plurality of oligonucleotides covering the entire sequence of one strand of the desired product and have a partial sequence overlap to the adjacent oligonucleotide(s), and wherein amplification is performed with universal forward and reverse primers, and through amplification cycling gradually results in full-length desired product that can then undergo dilution, sequence screening, and further amplification that results in the desired gene block end product.

DETAILED DESCRIPTION OF THE INVENTION

Figure 1:
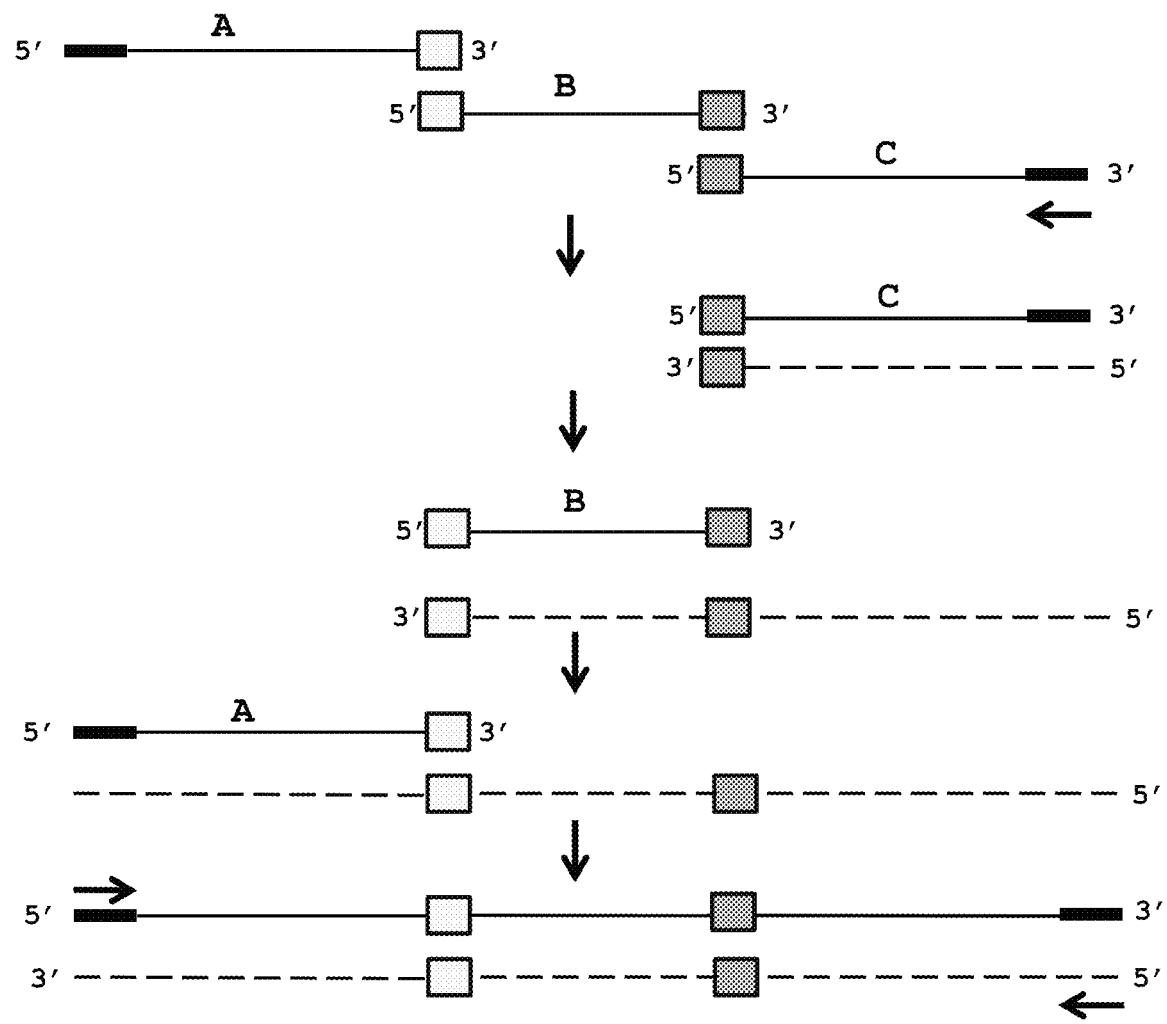
FIG. 1 is an illustration of top-strand PCR gene assembly. The upper portion, A, represents the first cycle of PCR, B the second cycle, and C is the desired full-length product.

Aspects of this invention relate to methods for synthesis of synthetic nucleic acid elements that may comprise genes or gene fragments. More specifically, the methods of the invention include methods of high fidelity oligonucleotide synthesis, the methods of use of high fidelity oligonucleotide synthesis in assembly/amplification methods such as top-strand PCR, and methods of gene assembly that yield a desired sequence, a gene block, through dilution of crude synthesized gene product, sequence verification and subsequent amplification.

The term "oligonucleotide," as used herein, refer to polydeoxyribonucleotides (containing 2-deoxy-D-ribose), polyribonucleotides (containing D-ribose), and to any other type of polynucleotide which is an N glycoside of a purine or pyrimidine base. There is no intended distinction in length between the terms "nucleic acid", "oligonucleotide" and "polynucleotide", and these terms can be used interchangeably. These terms refer only to the primary structure of the molecule. Thus, these terms include double- and single-stranded DNA, as well as double- and single-stranded RNA, or double- and single-stranded oligonucleotides containing both RNA and DNA. For use in the present invention, an oligonucleotide also can comprise nucleotide analogs in which the base, sugar or phosphate backbone is modified as well as non-purine or non-pyrimidine nucleotide analogs.

The terms "raw material oligonucleotide" and "gene sub-blocks" are used interchangeably in this application and refer to the initial oligonucleotide material that is further processed, synthesized, combined, joined, modified, transformed, purified or otherwise refined to form the basis of another oligonucleotide product. The raw material oligonucleotides are typically, but not necessarily, the oligonucleotides that are directly synthesized using phosphoramidite chemistry.

The oligonucleotides used in the inventive methods can be synthesized using any of the methods of enzymatic or chemical synthesis known in the art, although phosphoramidite chemistry is the most common. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648). High fidelity oligonucleotides are required in some embodiments of the methods of the present invention, and therefore array or microfluidic oligonucleotide synthesis will not always be compatible.

In one embodiment of the present invention, the oligonucleotides that are used for gene synthesis methods are high-fidelity oligonucleotides (average coupling efficiency is greater than 99.2%, or more preferably 99.5%). In one embodiment, the high-fidelity nucleotides are between 40-200 bases long. In a further embodiment the high-fidelity oligonucleotide is between 75-200 bases, and in a further embodiment 100-190 bases. High-fidelity oligonucleotides are available commercially, even at greater lengths (see Ultramer® oligonucleotides from Integrated DNA Technologies, Inc.). Alternatively, a novel method of the present invention is the use of low-CPG load solid supports that provide synthesis of high-fidelity oligonucleotides while reducing reagent use. Solid support membranes are used wherein the composition of CPG in the membranes is no more than 8% of the membrane by weight. Membranes known in the art are typically 20-50% (see for example, Ngo et al., U.S. Pat. No. 7,691,316). In a further embodiment, the composition of CPG in the membranes is no more than 5% of the membrane. The membranes offer scales as low as subnanomolar scales that are ideal for the amount of oligonucleotides used as the building blocks for gene synthesis. Less reagent amounts are necessary to perform synthesis using these novel membranes. The membranes can provide as low as 100-picomole scale synthesis or less. The low-CPG membranes offer higher fidelity of array synthesis while still allowing for lower reagent use. Lower-CPG membranes are most practical when used to synthesize oligonucleotides greater than 50 bases, or further, greater than 75 bases.

Other methods are known in the art to produce high-fidelity oligonucleotides. Enzymatic synthesis or the replication of existing PCR products traditionally has lower error rates than chemical synthesis of oligonucleotides due to convergent consensus within the amplifying population. However, further optimization of the phosphoramidite chemistry can achieve even greater quality oligonucleotides, which improves any gene synthesis method. A great number of advances have been achieved in the traditional four-step phosphoramidite chemistry since it was first described in the 1980's (see for example, Sierzchala, et al. *J. Am. Cem. Soc.*, 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., *Nucleosides, Nucleotides, and Nucleic Acids,* 24 (5-7), 1037-1041 (2005) for improved synthesis of longer oligonucleotides through the use of large-pore CPG; and Damha et al., *NAR*, 18, 3813-3821 (1990) for improved derivitization).

Regardless of the type of synthesis, the resulting oligonucleotides may then form the smaller building blocks for longer oligonucleotides. As referenced earlier, the smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligos that are homologous to the forward strand at the 5' end of the gene and against the reverse strand at the 3' end of the gene.

One method of the present invention provides an alternative method of synthesis of the smaller oligonucleotides. In this method, top-strand PCR (TSP), a plurality of oligonucleotides span the entire length of a desired product and are partially complementary to the adjacent oligonucleotide(s) (see FIG. 1). Amplification is performed with universal forward and reverse primers, and through multiple cycles of amplification a full-length desired product is formed. This product can then undergo dilution, sequence screening, and further amplification that results in the desired gene block end product.

In one method of TSP, the set of smaller oligonucleotides ("gene sub-blocks") that will be combined to form the full-length desired product are between 40-200 bases long. In a further embodiment the oligonucleotide is between 75-200 bases, and in a further embodiment 100-190 bases. The gene sub-blocks overlap each other by at least 15-20 bases. For practical purposes, the overlap region should be at a minimum long enough to ensure specific annealing of gene sub-blocks and have a high enough melting temperature ($T_m$) to anneal at the reaction temperature employed. The overlap can extend to the point where a given gene sub-block is completely overlapped by adjacent gene sub-blocks. The amount of overlap does not seem to have any effect on the quality of the final product. The first and last oligonucleotide building block in the assembly should contain binding sites for forward and reverse amplification primers. In one embodiment, the overlap regions contain the same sequence of complementarity to allow for the use of universal primers.

Applicants have discovered that although intuitively more cycles of TSP (e.g., 30 cycles) would produce a greater percent of full-length molecules, surprisingly a greater percent of correct full-length molecules (i.e., assembled DNA strand having the desired sequence without error) is produced using a low number of cycles (about 15 cycles). After the initial TSP reaction of ~15 cycles, the product can then be diluted 10-fold to 1000-fold, wherein the product is amplified again in 20-30 cycles of PCR to increase mass yield of the desired product.

Methods of mitigating synthesis errors are known in the art, and they optionally could be incorporated into methods of the present invention. The error correction methods include, but are not limited to, circularization methods wherein the properly assembled oligonucleotides are circularized while the other product remain linear and was enzymatically degraded (see Bang and Church, *Nat. Methods,* 5, 37-39 (2008)). The mismatches can be degraded using mismatch-cleaving endonucleases. Another error correction method utilizes MutS protein that binds to mismatches, thereby allowing the desired product to be separated (see Carr, P. A. et al. *Nucleic Acids Res.* 32, e162 (2004)). Other mismatch nucleases include those in the CEL nuclease family (see Surveyor® Nuclease, Transgenomics), or RES I (see Errase™ synthetic gene error correction kit, Novici). When error correction is used, the amount of remaining product may be small, and therefore a round of rescue PCR can be performed to amplify the desired product.

Whether the gene sub-blocks are combined through TSP or another form of assembly, the full-length product is diluted, typically to 0.25 to 10 copies per reaction well, and then amplified to result in a large amount of homogeneous, desired double-stranded product ("gene block"). In a further embodiment, the synthesized oligonucleotides are diluted to 1-5 copies of the synthesized oligonucleotide per reaction well, and in a further embodiment the synthesized oligonucleotides are diluted to 2-4 copies per reaction well.

The dilution and amplification steps replace the conventional, time-consuming, labor-intensive in vivo cloning procedures traditionally employed, which are well known in the art. Some dilution methods are known in the art (see Yehezkel et al., *Nucleic Acids Research,* vol. 36, no. 17, e107 (2008)), but they have been inefficient. The goal of dilution PCR is to dilute the initial product, which is a mixture of desired perfect product and undesired imperfect products, into reaction wells to a dilution that best assures that an adequate amount of reaction wells contain the desired product. If the mixture is too dilute then there are undesired empty wells, and if the mixture is not diluted enough then too many wells contain multiple template molecules (product of desired sequence plus defective product containing an undesired sequence). Since DNA sequencing is a significant portion of gene synthesis cost, typical dilutions would normally be less than one molecule per well, and even as low as 0.2 molecules per well to ensure clonality.

In the methods of the present invention, dilution conditions can be used that allow for as much as 1-5 copies of oligonucleotides/well to be present. Because the fidelity of the gene sub-blocks made using the methods of the present invention is so high, the product being diluted is weighted heavily to contain a high percentage of correct sequence material. Therefore, if a given well has 4 molecules, there is still a high likelihood that the amplified product will be of the correct sequence. Diluting to an average copy of 1-5, or more preferably 2-4, reduces the number of empty wells and increases the efficiency of the manufacturing process.

The resulting product after dilution and amplification is then directly sequence verified without the traditional need to first clone the product into a plasmid vector and expand in a bacterial host. The final product is a desired, sequence verified gene block. The gene blocks can then later be cloned through methods well-known in the art, such as isothermal assembly (e.g., Gibson et al. *Science,* 319, 1215-1220 (2008)); ligation-by-assembly or restriction cloning (e.g., Kodumal et al., *Proc. Natl. Acad. Sci. U.S.A.,* 101, 15573-15578 (2004) and Viallalobos et al., *BMC Bioinformatics,* 7, 285 (2006)); TOPO TA cloning (Invitrogen/Life Tech.); blunt-end cloning; and homologous recombination (e.g., Larionov et al., *Proc. Natl. Acad. Sci. U.S.A.,* 93, 491-496). The gene blocks can be cloned into many vectors known in the art, including but not limited to pUC57, pBluescriptII (Stratagene), pET27, Zero Blunt TOPO (Invitrogen), psiCHECK-2, pIDTSMART (Integrated DNA Technologies, Inc.), and pGEM T (Promega).

The above methods can be re-ordered or altered, or further steps can be incorporated to optimize the end product, particularly if the known end-product is shorter or longer. For example, in one embodiment where the desired end product is a gene block smaller than 500 bases, the initial steps would be to synthesize the gene sub-blocks, perform PCR (e.g., TSP), then dilute and amplify. The resulting product is then treated with error correction and then undergoes amplification, such as PCR. Optionally, the product undergoes a second dilution step and amplification. The end product then is re-amplified with sequence-specific primers if there is a need to remove universal sequences inserted for use in earlier amplification steps.

For longer desired products (i.e., greater than 500 bases), a number of options are available to manufacture the longer end product. In one embodiment, longer TSP-assembled starting material is used. In another embodiment, two or more smaller products are used, and those products undergo isothermal assembly. Those products could be combined with other products to make even longer gene blocks. In another embodiment, two or more TSP-assembled products that undergo isothermal assembly. In another embodiment, a set of oligonucleotides of about 60 bases in length, wherein the oligonucleotides overlap with adjacent oligonucleotides to cover a 1-2 kb sequence length, are combined and undergo isothermal assembly.

The gene blocks can be used in a variety of applications, not limited to but including protein expression (recombinant antibodies, novel fusion proteins, codon optimized short proteins, functional peptides—catalytic, regulatory, binding domains), microRNA genes, template for in vitro transcription (IVT), shRNA expression cassettes, regulatory sequence cassettes, micro-array ready cDNA, gene variants and SNPs, DNA vaccines, standards for quantitative PCR and other assays, and functional genomics (mutant libraries and unrestricted point mutations for protein mutagenesis, and deletion mutants). The ease of synthesizing large genes or gene segments using gene blocks allows for the synthesis of a set of large segments/genes wherein one or more gene blocks remain constant while one or more gene blocks varies.

The following examples further illustrate the invention but, of course, should not be construed as in any way limiting its scope.

Example 1

This example illustrates an assembly of gene sub-blocks into a product containing desired gene blocks.

A 935 bp gene block comprising 6 synthetic oligonucleotide subunits and a 1155 bp gene block comprising 8 synthetic oligonucleotide subunits were assembled. The 8-oligonucleotide gene block is an extension of the smaller 935 bp 6-oligonucleotide gene block sequence having an additional 220 bp at the 3'-end. Therefore both gene blocks use the same 6 component oligonucleotides in assembly, and the 8-oligonucleotide gene block also includes oligonucleotides 7 and 8. The sequences of the gene blocks, the component oligonucleotides, the universal forward primer, the universal reverse primer (8-block) and gene specific reverse primers (6-block). Gene blocks were assembled using component oligonucleotides having an unmodified 3'-end, having 6 additional non-templated T bases added to the 3'-end of each oligonucleotide (T-blocked), having 8 additional non-templated T bases plus a terminal C3 spacer (propanediol) (T+C3-blocked), or having a terminal C3 spacer (propanediol) added to the end of each oligonucleotide. The different end-blocked versions of assembly will test whether extension from the 3'-end of component oligonucleotides is necessary during TSP. The following sequences were used:

```
935 base Gene Block (SEQ ID No. 1):
CGACACTGCTCGATCCGCTCGCACCAAATCCAGATGACACAGAGTCCGTC
CTCGCTTTCTGCGTCCCTGGGCGATCGTGTAACCATTACATGTCAGGCTA
GTCGCGGCATCGGAAAAGACTTAAATTGGTACCAGCAGAAAGCGGGCAAA
GCCCCTAAACTGCTGGTGAGCGATGCCAGCACATTGGAGGGCGGCGTTCC
GTCACGTTTCAGTGGTAGCGGCTTCCATCAAAATTTCAGCTTAACCATCT
CCAGTCTGCAGGCCGAGGATGTGGCTACCTATTTCTGCCAGCAGTATGAA
ACTTTCGGCCAGGGAACCAAAGTCGATATTAAAAGGTCGACGGTCGCGCC
GAGCGTGTTTATTTTCCCGCCGTCTGATGAACAGCTGAAATCAGGCACCG
CATCGGTGGTTTGCCTGCTGAACAATTTTTATCCGCGTGAAGCGAAAGTT
CAGTGGAAAGTGGATAACGCCCTGCAGAGCGGTAATTCGCAAGAAAGCGT
CACCGAACAAGATTCTAAAGACAGTACGTACTCCCTGAGCTCTACCCTGA
CGCTGTCAAAAGCAGATTACGAAAAACATAAAGTGTACGCTTGCGAAGTT
ACCCACCAAGGCCTGAGTTCCCCGGTTACGAAATCCTTCAACCGTGGCGA
ATGTTAAGCTGGGGATCCTCTAGAGGTTGAGGTGATTTTATGAAGAAAAA
CATTGCGTTTCTGCTGGCGAGCATGTTTGTGTTCTCTATCGCCACCAATG
CGTATGCCCTCGAGCAAGTGCAATTGGTCCAGTCGGGCGCGGAAGTTAAG
AAACCGGGGCCTCTGTGAAAGTCTCCTGCAAAGCCTCTGGTTATACGTT
TACAGGCTACTATATGCACTGGGTGCGTCAAGCCCCGGGTCAAGGTCTGG
AGTGGATGGGTTGGATTAACCCGAACTCCGGTGGT 1155 base Gene Block (SEQ ID No. 2):
CGACACTGCTCGATCCGCTCGCACCAAATCCAGATGACACAGAGTCCGTC
CTCGCTTTCTGCGTCCCTGGGCGATCGTGTAACCATTACATGTCAGGCTA
GTCGCGGCATCGGAAAAGACTTAAATTGGTACCAGCAGAAAGCGGGCAAA
GCCCCTAAACTGCTGGTGAGCGATGCCAGCACATTGGAGGGCGGCGTTCC
GTCACGTTTCAGTGGTAGCGGCTTCCATCAAAATTTCAGCTTAACCATCT
CCAGTCTGCAGGCCGAGGATGTGGCTACCTATTTCTGCCAGCAGTATGAA
ACTTTCGGCCAGGGAACCAAAGTCGATATTAAAAGGTCGACGGTCGCGCC
GAGCGTGTTTATTTTCCCGCCGTCTGATGAACAGCTGAAATCAGGCACCG
CATCGGTGGTTTGCCTGCTGAACAATTTTTATCCGCGTGAAGCGAAAGTT
CAGTGGAAAGTGGATAACGCCCTGCAGAGCGGTAATTCGCAAGAAAGCGT
CACCGAACAAGATTCTAAAGACAGTACGTACTCCCTGAGCTCTACCCTGA
CGCTGTCAAAAGCAGATTACGAAAAACATAAAGTGTACGCTTGCGAAGTT
ACCCACCAAGGCCTGAGTTCCCCGGTTACGAAATCCTTCAACCGTGGCGA
ATGTTAAGCTGGGGATCCTCTAGAGGTTGAGGTGATTTTATGAAGAAAAA
CATTGCGTTTCTGCTGGCGAGCATGTTTGTGTTCTCTATCGCCACCAATG
CGTATGCCCTCGAGCAAGTGCAATTGGTCCAGTCGGGCGCGGAAGTTAAG
AAACCGGGGCCTCTGTGAAAGTCTCCTGCAAAGCCTCTGGTTATACGTT
TACAGGCTACTATATGCACTGGGTGCGTCAAGCCCCGGGTCAAGGTCTGG
AGTGGATGGGTTGGATTAACCCGAACTCCGGTGGTACCAACTATGCGCAG
AAATTCCAGGGTCGCGTCACGATGACTCGCGACACGTCAATTAGTACCGC
GTACATGGAGTTATCGCGTTTACGTAGTGACGACACCGCCGTATACTACT
GTGCGCGTGCTCAGAAACGCGGCCGTTCTGAATGGGCGTACGCACATTGG
GGTCAAGGCACCCTGGTGACCGTGAGTAGTGGATCGACGAGAGCAGCGCG
ACTGG Component oligonucleotide 1 (SEQ ID No. 3):
CGACACTGCTCGATCCGCTCGCACCAAATCCAGATGACACAGAGTCCGTC
CTCGCTTTCTGCGTCCCTGGGCGATCGTGTAACCATTACATGTCAGGCTA
GTCGCGGCATCGGAAAAGACTTAAATTGGTACCAGCAGAAAGCGGGCAAA
GCCCCTAAACTGCTGGTGAGCGATGCCAGCACATTGGAG Component oligonucleotide 2 (SEQ ID No. 4):
CTGGTGAGCGATGCCAGCACATTGGAGGGCGGCGTTCCGTCACGTTTCAG
TGGTAGCGGCTTCCATCAAAATTTCAGCTTAACCATCTCCAGTCTGCAGG
CCGAGGATGTGGCTACCTATTTCTGCCAGCAGTATGAAACTTTCGGCCAG
GGAACCAAAGTC Component oligonucleotide 3 (SEQ ID No. 5):
GCAGTATGAAACTTTCGGCCAGGGAACCAAAGTCGATATTAAAAGGTCGA
CGGTCGCGCCGAGCGTGTTTATTTTCCCGCCGTCTGATGAACAGCTGAAA
TCAGGCACCGCATCGGTGGTTTGCCTGCTGAACAATTTTTATCCGCGTGA
AGCGAAAGTTCAGTGGAAAGTGGATAACGCCCTGCAGAG Component oligonucleotide 4 (SEQ ID No. 6):
GTTCAGTGGAAAGTGGATAACGCCCTGCAGAGCGGTAATTCGCAAGAAAG
CGTCACCGAACAAGATTCTAAAGACAGTACGTACTCCCTGAGCTCTACCC
TGACGCTGTCAAAAGCAGATTACGAAAAACATAAAGTGTACGCTTGCGAA
GTTACCCACCAAGGCCTGAGTTCCCCGGTTACGAAATCC Component oligonucleotide 5 (SEQ ID No. 7):
CCAAGGCCTGAGTTCCCCGGTTACGAAATCCTTCAACCGTGGCGAATGTT
AAGCTGGGGATCCTCTAGAGGTTGAGGTGATTTTATGAAGAAAAACATTG
CGTTTCTGCTGGCGAGCATGTTTGTGTTCTCTATCGCCACCAATGCGTAT
GCCCTCGAGCAAGTGCAATTGGTC Component oligonucleotide 6 (SEQ ID No. 8):
CGTATGCCCTCGAGCAAGTGCAATTGGTCCAGTCGGGCGCGGAAGTTAAG
AAACCGGGGCCTCTGTGAAAGTCTCCTGCAAAGCCTCTGGTTATACGTT
TACAGGCTACTATATGCACTGGGTGCGTCAAGCCCCGGGTCAAGGTCTGG
AGTGGATGGGTTGGATTAACCCGAACTCCGGTGGT
```

Component oligonucleotide 7 (SEQ ID No. 9):
GGGTTGGATTAACCCGAACTCCGGTGGTACCAACTATGCGCAGAAATTCC

AGGGTCGCGTCACGATGACTCGCGACACGTCAATTAGTACCGCGTACATG

GAGTTATCGCGTTTACGTAGTG

Component oligonucleotide 8 (SEQ ID No. 10):
TACCGCGTACATGGAGTTATCGCGTTTACGTAGTGACGACACCGCCGTAT

ACTACTGTGCGCGTGCTCAGAAACGCGGCCGTTCTGAATGGGCGTACGCA

CATTGGGGTCAAGGCACCCTGGTGACCGTGAGTAGTGGATCGACGAGAGC

AGCGCGACTGG

Universal For primer 5'-phos (SEQ ID No. 11):
/5Phos/CGACACTGCTCGATCCGCTCGCACC

Universal Rev primer 5'-phos (SEQ ID No. 12):
/5Phos/CCAGTCGCGCTGCTCTCGTCGATCC

Gene Specific Rev primer (SEQ ID No. 13):
/5Phos/ACCACCGGAGTTCGGGTTAATCCAACC

The component oligonucleotides were assembled by TSP using the following reaction mixture and conditions:
50/100 nM component oligonucleotides 1-6/8
50/100 nM forward primer
200 nM reverse primer
0.02 U/uL KOD Hot-Start DNA polymerase (Novagen)
1× buffer for KOD Hot Start DNA polymerase (Novagen)
1.5 mM MgSO$_4$
0.8 mM dNTPs (0.2 mM each)
Cycling conditions: 95° C.$^{3:00}$ (95° C.$^{0:20}$–70° C.$^{0:30}$)×15, 20, 25, or 30 cycles Additionally, several sets of otherwise identical component oligonucleotides were used in TSP assembly wherein the 3' ends are either unblocked or blocked with a 6-residue poly-T; a C3 spacer; or a 8-residue poly-T plus a C3 spacer. After the TSP cycles, the resulting products were diluted 100-fold in water, and then underwent a further step of PCR containing 200 nM each of the universal forward primer and 200 nM of the universal reverse primer (8-block) or gene specific reverse primer (6-block) (cycling conditions: 95° C.$^{3:00}$ (95° C.$^{0:20}$–70° C.$^{0:30}$)×30 cycles). The resulting gene block was run on a 1.2% agarose gel at 100V for 1 hour 30 minutes.

Figure 2A:
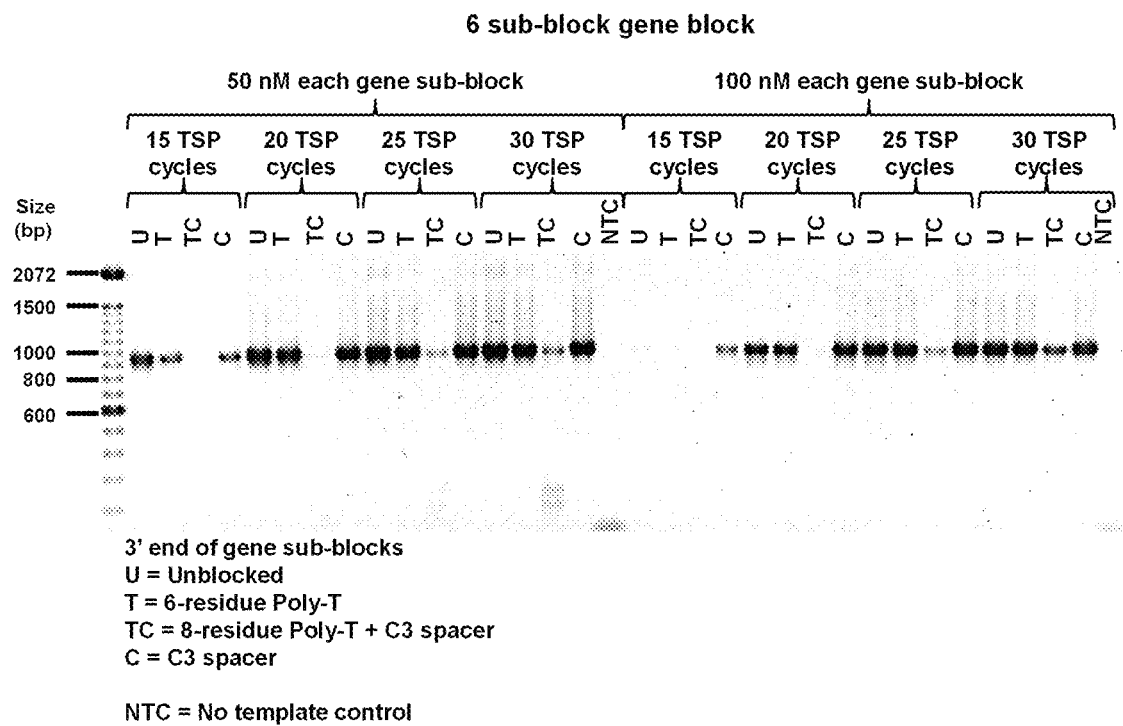
FIG. 2A is a gel showing the successful generation of the desired gene block assembled using six gene sub-blocks.
Figure 2B:
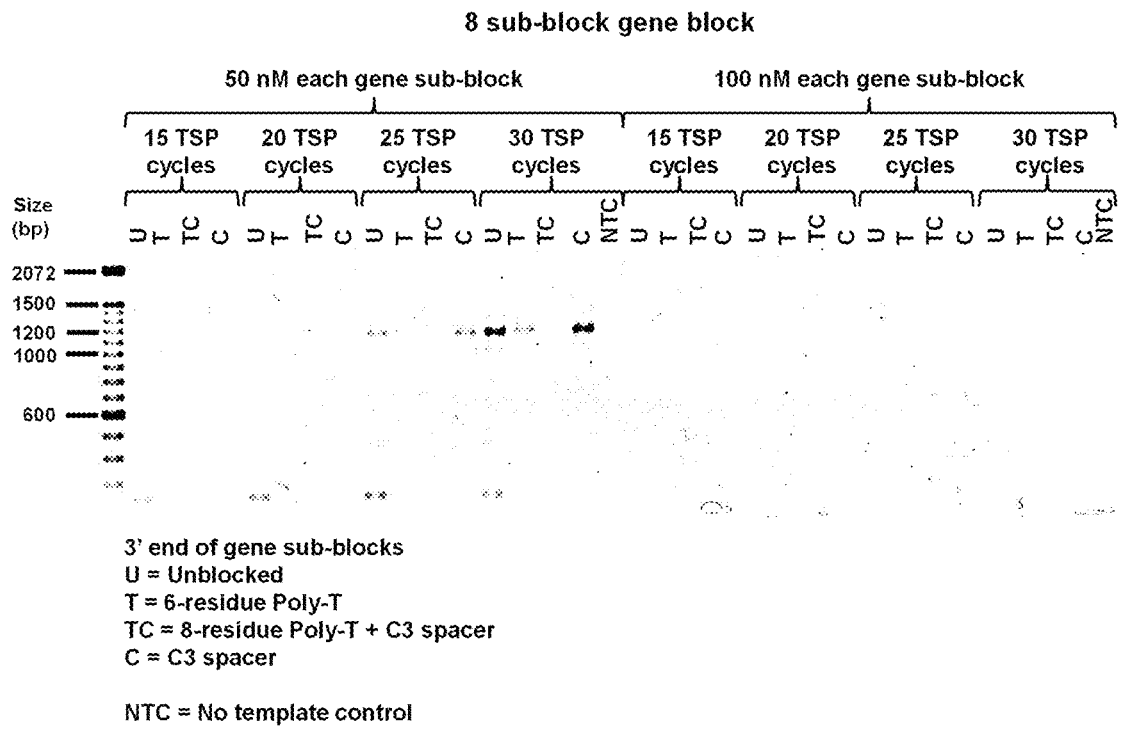
FIG. 2B is a gel showing the successful generation of the desired gene block assembled using eight gene sub-blocks.
Figure 3A:
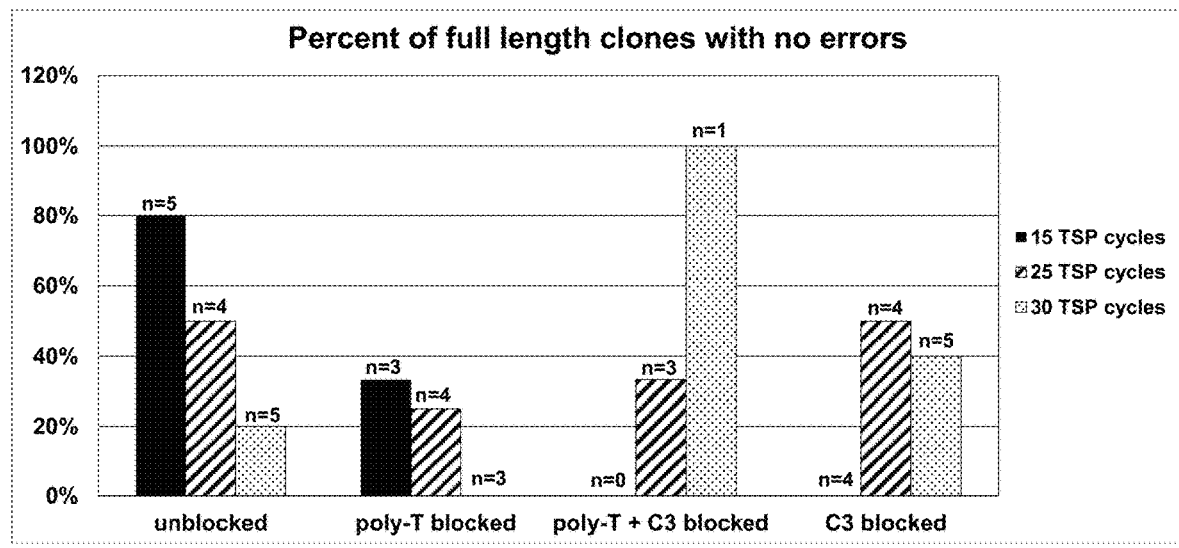
FIGS. 3A and 3B graphically represent the amount of full length clones with no errors for each set of reactions.
Figure 3B:
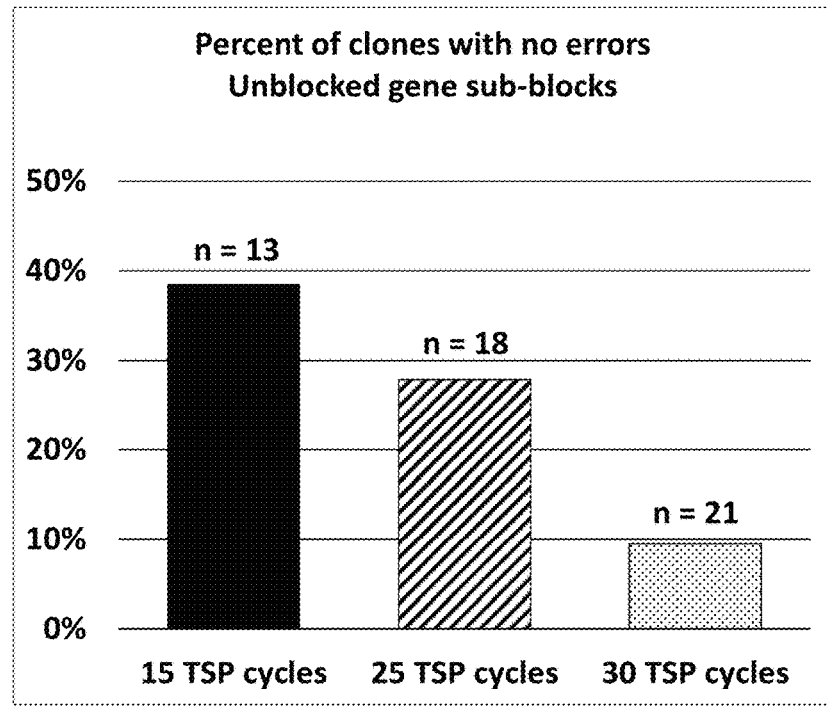

FIG. 2A is a picture of the resulting gel of the 935-base 6-component oligonucleotides gene block, and FIG. 2B is the resulting gel for the 1155 base 8-component oligonucleotides gene block. Notably, at 15 TSP cycles the desired product is present, particularly using the unblocked component oligonucleotides. The 50 nM 6-block gene blocks were blunt cloned into a pUC19 vector and sequence verified using Sanger sequencing using a 3730xl sequencer (Life Technologies-Applied Biosystems). FIG. 3A graphically represents the percent of full length clones with no errors for each set of reactions. FIG. 3B represents the percent of all clones with no errors after sequencing additional clones generated using unblocked component oligonucleotides. Although all conditions produce full-length clones with no errors, surprisingly the low cycle number unblocked component oligonucleotides was the most robust and yielded the highest percentage of correct final products.

Example 2

This example demonstrates that various lengths, concentrations and numbers of component oligonucleotides and varying component oligonucleotide overlap conditions can be used to successfully produce full length gene blocks.

Figure 4:
FIG. 4 depicts the 3 gene sub-block designs used to assemble the gene blocks according to Example 2.
Figure 4:
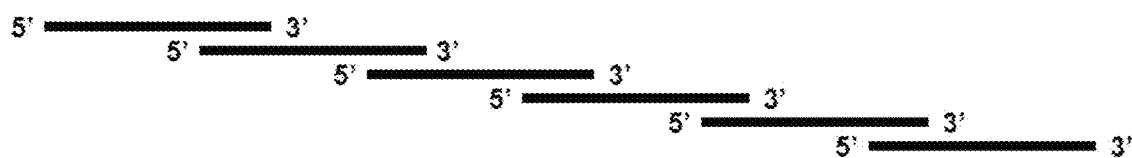
Figure 4:
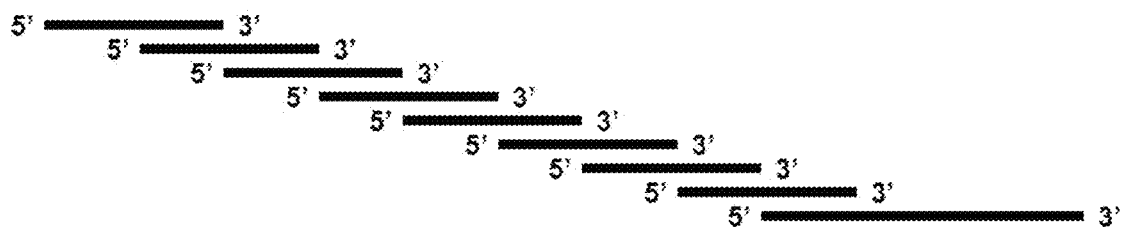

FIG. 4 illustrates the three overlap designs used in this example. Design 1 uses component oligonucleotides that are 115-185 nucleotides in length. Design 2 uses shorter component oligonucleotides, between 54-125 nucleotides. Design 3 uses 100 nucleotide-long component oligonucleotides (the last oligonucleotide may be shorter or longer than 100 nucleotides depending on final gene block length), and employs a complete overlap design wherein the adjacent oligonucleotides completely overlap each non-terminal component.

The following are the sequences of the desired gene blocks and component oligonucleotides. The same universal For and Rev primers from Example 1 (SEQ ID Nos. 11-12) were used.

Gene Block A (SEQ ID No. 14):
CGACACTGCTCGATCCGCTCGCACCTTTCTGGCATGAGGTCACTGACAGC

CCTCTGGACAACACAGCTTATTTATTGGTCTCTCATTCTCCCATCCCCAC

TCCTCCTTTCTTCCCTCTCTCCACCAGAGCGATGGCGTCACCGGCCCATC

CTCCAAGCCGGACTGCCGGCAAATGCCTCCACAGTGGTCGGAGGAGACGT

AGAGTTTGTCTGCAAGGTTTACAGTGATGCCCAGCCCCACATCCAGTGGA

TCAAGCACGTGGAAAAGAACGGCAGTAAATACGGGCCCGACGGGCTGCCC

TACCTCAAGGTTCTCAAGGTGAGGACTTTCTGAATCTAAAGGTACCCACA

ACTGGGGTCTCCTTCATGGGTTTGGCCACAGGTTCTTTGATTTCCTGTTG

GAGTTGAGAGAGGATGATTCTCTTTTTTGACTAGCCAGCAGAGAGTGTTC

TAAGGGGATCGACGAGAGCAGCGCGACTGG

Gene Block B (SEQ ID No. 15):
CGACACTGCTCGATCCGCTCGCACCGCACCTGTACGATCACTGAACTGCA

GAATCTGGGATGTTAACCAGAAGACCTTCTATCTGAGGAACAACCAACTA

GTTGCTGGATACTTGCAAGGACCAAATGTCAATTTAGAAGAAAAGTTCGA

CATGTCCTTTGTAGAAGGACATGAAAGTAATGACAAAATACCTGTGGCCT

TGGGCCTCAAGGAAAAGAATCTGTACCTGTCCTGCGTGTTGAAAGATGAT

GAACCCACTCTACAGCTGGAGGCTGTAAATCCCAAAAATTACCCAAAGAG

GAAGATGGAAAAGCGATTTGTCTTCAACAAGATAGATTCAGGCCCAACCA

CATCATTTGAGTCTGCCCAGTTCCCCAACTGGTTCCTCTGCACAGCGATG

GAAGCTGACCAGCCCGTCAGCCTCACCAATATGCCTGACGAAGGCGTCAT

GGTCACCAAATTCTACATGCAATTTGTGTCTTCCGGATCGACGAGAGCAG

CGCGACTGG

Gene Block C (SEQ ID No. 16):
CGACACTGCTCGATCCGCTCGCACCCATATGGCCAAGCTGACCAGCGCCG

TTCCGGTGCTCACCGCGCGCGACGTCGCCGGAGCGGTCGAGTTCTGGACC

GACCGGCTCGGGTTCTCCCGGGACTTCGTGGAGGACGACTTCGCCGGTGT

GGTCCGGGACGACGTGACCCTGTTCATCAGCGCGGTCCAGGACCAGGTAA

GACGCAATTCTGCTGTGCACGTGCCAATGCCGCTGCCCCCCAGCGCATTG

GCTCACCATCGCCATCGCCATTGCTGCTGCAGGTGGTGCCGGACAACACC

CTGGCCTGGGTGTGGGTGCGCGGCCTGGACGAGCTGTACGCCGAGTGGTC

GGAGGTCGTGTCCACGAACTTCCGGGACGCCTCCGGGCCGGCCATGACCG

AGATCGGCGAGCAGCCGTGGGGGCGGGAGTTCGCCCTGCGCGACCCGGCC

GGCAACTGCGTGCACTTCGTGGCCGAGGAGCAGGACTAAGGATCCGGATC

GACGAGAGCAGCGCGACTGG

Gene Block A Design 1 Component oligonucleotide 1
(SEQ ID No. 17):
CGACACTGCTCGATCCGCTCGCACCTTTCTGGCATGAGGTCACTGACAGC

CCTCTGGACAACACAGCTTATTTATTGGTCTCTCATTCTCCCATCCCCAC

TCCTCCTTTCTTCCCTCTCTCCACCAGAGCGATGGCGTCACCGGCCCATC

CTCCAAGCCGGACTGCCGGCAAATGCCTCCACAG

Gene Block A Design 1 Component oligonucleotide 2
(SEQ ID No. 18):
GGACTGCCGGCAAATGCCTCCACAGTGGTCGGAGGAGACGTAGAGTTTGT

CTGCAAGGTTTACAGTGATGCCCAGCCCCACATCCAGTGGATCAAGCACG

TGGAAAAGAACGGCAGTAAATACGGGCCCGACGGGCTGCCCTACCTCAAG

GTTCTCAAGGTGAGGACTTTCTGAATCTAAAGG

Gene Block A Design 1 Component oligonucleotide 3
(SEQ ID No. 19):
CCTCAAGGTTCTCAAGGTGAGGACTTTCTGAATCTAAAGGTACCCACAAC

TGGGGTCTCCTTCATGGGTTTGGCCACAGGTTCTTTGATTTCCTGTTGGA

GTTGAGAGAGGATGATTCTCTTTTTTGACTAGCCAGCAGAGAGTGTTCTA

AGGGGATCGACGAGAGCAGCGCGACTGG

Gene Block A Design 2 Component oligonucleotide 1
(SEQ ID No. 20):
CGACACTGCTCGATCCGCTCGCACCTTTCTGGCATGAGGTCACTGACAGC

CCTCTGG

Gene Block A Design 2 Component oligonucleotide 2
(SEQ ID No. 21):
GGCATGAGGTCACTGACAGCCCTCTGGACAACACAGCTTATTTATTGGTC

TCTCATTCTCCCATCCCCACTCCTCCTTTCTTCCCTCTCTCCACCAGAGC

GATGGCGTCACCGGCCCATCC

Gene Block A Design 2 Component oligonucleotide 3
(SEQ ID No. 22):
CGATGGCGTCACCGGCCCATCCTCCAAGCCGGACTGCCGGCAAATGCCTC

CACAGTGGTCGGAGGAGACGTAGAGTTTGTCTGCAAGGTTTACAGTGATG

Gene Block A Design 2 Component oligonucleotide 4
(SEQ ID No. 23):
GGAGACGTAGAGTTTGTCTGCAAGGTTTACAGTGATGCCCAGCCCCACAT

CCAGTGGATCAAGCACGTGGAAAAGAACGGCAGTAAATACGGGCCCGACG

GGCTGCCCTACC

Gene Block A Design 2 Component oligonucleotide 5
(SEQ ID No. 24):
GCCCGACGGGCTGCCCTACCTCAAGGTTCTCAAGGTGAGGACTTTCTGAA

TCTAAAGGTACCCACAACTGGGGTCTCCTTCATGGGTTTGGCCACAGGTT

CTTTGATTTCCTGTTGGAG

Gene Block A Design 2 Component oligonucleotide 6
(SEQ ID No. 25):
GGTTTGGCCACAGGTTCTTTGATTTCCTGTTGGAGTTGAGAGAGGATGAT

TCTCTTTTTTGACTAGCCAGCAGAGAGTGTTCTAAGGGGATCGACGAGAG

CAGCGCGACTGG

Gene Block A Design 3 Component oligonucleotide 1
(SEQ ID No. 26):
CGACACTGCTCGATCCGCTCGCACCTTTCTGGCATGAGGTCACTGACAGC

CCTCTGGACAACACAGCTTATTTATTGGTCTCTCATTCTCCCATCCCCAC

Gene Block A Design 3 Component oligonucleotide 2
(SEQ ID No. 27):
CCTCTGGACAACACAGCTTATTTATTGGTCTCTCATTCTCCCATCCCCAC

TCCTCCTTTCTTCCCTCTCTCCACCAGAGCGATGGCGTCACCGGCCCATC

Gene Block A Design 3 Component oligonucleotide 3
(SEQ ID No. 28):
TCCTCCTTTCTTCCCTCTCTCCACCAGAGCGATGGCGTCACCGGCCCATC

CTCCAAGCCGGACTGCCGGCAAATGCCTCCACAGTGGTCGGAGGAGACGT

Gene Block A Design 3 Component oligonucleotide 4
(SEQ ID No. 29):
CTCCAAGCCGGACTGCCGGCAAATGCCTCCACAGTGGTCGGAGGAGACGT

AGAGTTTGTCTGCAAGGTTTACAGTGATGCCCAGCCCCACATCCAGTGGA

Gene Block A Design 3 Component oligonucleotide 5
(SEQ ID No. 30):
AGAGTTTGTCTGCAAGGTTTACAGTGATGCCCAGCCCCACATCCAGTGGA

TCAAGCACGTGGAAAAGAACGGCAGTAAATACGGGCCCGACGGGCTGCCC

Gene Block A Design 3 Component oligonucleotide 6
(SEQ ID No. 31):
TCAAGCACGTGGAAAAGAACGGCAGTAAATACGGGCCCGACGGGCTGCCC

TACCTCAAGGTTCTCAAGGTGAGGACTTTCTGAATCTAAAGGTACCCACA

Gene Block A Design 3 Component oligonucleotide 7
(SEQ ID No. 32):
TACCTCAAGGTTCTCAAGGTGAGGACTTTCTGAATCTAAAGGTACCCACA

ACTGGGGTCTCCTTCATGGGTTTGGCCACAGGTTCTTTGATTTCCTGTTG

Gene Block A Design 3 Component oligonucleotide 8
(SEQ ID No. 33):
ACTGGGGTCTCCTTCATGGGTTTGGCCACAGGTTCTTTGATTTCCTGTTG

GAGTTGAGAGAGGATGATTCTCTTTTTTGACTAGCCAGCAGAGAGTGTTC

Gene Block A Design 3 Component oligonucleotide 9
(SEQ ID No. 34):
GAGTTGAGAGAGGATGATTCTCTTTTTTGACTAGCCAGCAGAGAGTGTTC

TAAGGGGATCGACGAGAGCAGCGCGACTGG

Gene Block B Design 1 Component oligonucleotide 1
(SEQ ID No. 35):
CGACACTGCTCGATCCGCTCGCACCGACACCTGTACGATCACTGAACTGCA

GAATCTGGGATGTTAACCAGAAGACCTTCTATCTGAGGAACAACCAACTA

GTTGCTGGATACTTGCAAGGACCAAATGTCAATTTAGAAG

Gene Block B Design 1 Component oligonucleotide 2
(SEQ ID No. 36):
GTTGCTGGATACTTGCAAGGACCAAATGTCAATTTAGAAGAAAAGTTCGA

CATGTCCTTTGTAGAAGGACATGAAAGTAATGACAAAATACCTGTGGCCT

TGGGCCTCAAGGAAAAGAATCTGTACCTGTCCTGCGTGTTGAAAGATGAT

GAACCCACTCTACAGCTGGAGGCTGTAAATCCC

Gene Block B Design 1 Component oligonucleotide 3
(SEQ ID No. 37):
GAACCCACTCTACAGCTGGAGGCTGTAAATCCCAAAAATTACCCAAAGAG

GAAGATGGAAAAGCGATTTGTCTTCAACAAGATAGATTCAGGCCCAACCA

CATCATTTGAGTCTGCCCAGTTCCCCAACTGGTTCCTCTGCACAGCGATG

GAAGCTG

Gene Block B Design 1 Component oligonucleotide 4
(SEQ ID No. 38):
CTGGTTCCTCTGCACAGCGATGGAAGCTGACCAGCCCGTCAGCCTCACCA

ATATGCCTGACGAAGGCGTCATGGTCACCAAATTCTACATGCAATTTGTG

TCTTCCGGATCGACGAGAGCAGCGCGACTGG

Gene Block B Design 2 Component oligonucleotide 1
(SEQ ID No. 39):
CGACACTGCTCGATCCGCTCGCACCGCACCTGTACGATCACTGAACTGCA

GAATCTGGGATGTTAACCAGAAG

Gene Block B Design 2 Component oligonucleotide 2
(SEQ ID No. 40):
CGATCACTGAACTGCAGAATCTGGGATGTTAACCAGAAGACCTTCTATCT

GAGGAACAACCAACTAGTTGCTGGATACTTGCAAGGACCAAATGTCAATT

TAGAAGAAAAGTTCGACATGTCC

Gene Block B Design 2 Component oligonucleotide 3
(SEQ ID No. 41):
ATGTCAATTTAGAAGAAAAGTTCGACATGTCCTTTGTAGAAGGACATGAA

AGTAATGACAAAATACCTGTGGCCTTGGGCCTCAAGG

Gene Block B Design 2 Component oligonucleotide 4
(SEQ ID No. 42):
ACCTGTGGCCTTGGGCCTCAAGGAAAAGAATCTGTACCTGTCCTGCGTGT

TGAAAGATGATGAACCCACTCTACAGCTGGAGGCTGTAAATCCC

Gene Block B Design 2 Component oligonucleotide 5
(SEQ ID No. 43):
GAACCCACTCTACAGCTGGAGGCTGTAAATCCCAAAAATTACCCAAAGAG

GAAGATGGAAAAGCGATTTGTCTTCAACAAGATAGATTCAGGCCCAACCA

CATCATTTGAGTCTGCCCAGTTCCC

Gene Block B Design 2 Component oligonucleotide 6
(SEQ ID No. 44):
AACCACATCATTTGAGTCTGCCCAGTTCCCCAACTGGTTCCTCTGCACAG

CGATGGAAGCTGACCAGCCCGTCAGCCTCACCAATATGCCTGACGAAGGC

Gene Block B Design 2 Component oligonucleotide 7
(SEQ ID No. 45):
GTCAGCCTCACCAATATGCCTGACGAAGGCGTCATGGTCACCAAATTCTA

CATGCAATTTGTGTCTTCCGGATCGACGAGAGCAGCGCGACTGG

Gene Block B Design 3 Component oligonucleotide 1
(SEQ ID No. 46):
CGACACTGCTCGATCCGCTCGCACCGCACCTGTACGATCACTGAACTGCA

GAATCTGGGATGTTAACCAGAAGACCTTCTATCTGAGGAACAACCAACTA

Gene Block B Design 3 Component oligonucleotide 2
(SEQ ID No. 47):
GAATCTGGGATGTTAACCAGAAGACCTTCTATCTGAGGAACAACCAACTA

GTTGCTGGATACTTGCAAGGACCAAATGTCAATTTAGAAGAAAAGTTCGA

Gene Block B Design 3 Component oligonucleotide 3
(SEQ ID No. 48):
AGTTGCTGGATACTTGCAAGGACCAAATGTCAATTTAGAAGAAAAGTTCG

ACATGTCCTTTGTAGAAGGACATGAAAGTAATGACAAAATACCTGTGGCC

Gene Block B Design 3 Component oligonucleotide
(SEQ ID No. 49):
ACATGTCCTTTGTAGAAGGACATGAAAGTAATGACAAAATACCTGTGGCC

TTGGGCCTCAAGGAAAAGAATCTGTACCTGTCCTGCGTGTTGAAAGATGA

Gene Block B Design 3 Component oligonucleotide 5
(SEQ ID No. 50):
CTTGGGCCTCAAGGAAAAGAATCTGTACCTGTCCTGCGTGTTGAAAGATG

ATGAACCCACTCTACAGCTGGAGGCTGTAAATCCCAAAAATTACCCAAAG

Gene Block B Design 3 Component oligonucleotide 6
(SEQ ID No. 51):
ATGAACCCACTCTACAGCTGGAGGCTGTAAATCCCAAAAATTACCCAAAG

AGGAAGATGGAAAAGCGATTTGTCTTCAACAAGATAGATTCAGGCCCAAC

Gene Block B Design 3 Component oligonucleotide 7
(SEQ ID No. 52):
GAGGAAGATGGAAAAGCGATTTGTCTTCAACAAGATAGATTCAGGCCCAA

CCACATCATTTGAGTCTGCCCAGTTCCCCAACTGGTTCCTCTGCACAGCG

Gene Block B Design 3 Component oligonucleotide 8
(SEQ ID No. 53):
CCACATCATTTGAGTCTGCCCAGTTCCCCAACTGGTTCCTCTGCACAGCG

ATGGAAGCTGACCAGCCCGTCAGCCTCACCAATATGCCTGACGAAGGCGT

Gene Block B Design 3 Component oligonucleotide 9
(SEQ ID No. 54):
GATGGAAGCTGACCAGCCCGTCAGCCTCACCAATATGCCTGACGAAGGCG

TCATGGTCACCAAATTCTACATGCAATTTGTGTCTTCCGGATCGACGAGA

GCAGCGCGACTGG

Gene Block C Design 1 Component oligonucleotide 1
(SEQ ID No. 55):
CGACACTGCTCGATCCGCTCGCACCCATATGGCCAAGCTGACCAGCGCCG

TTCCGGTGCTCACCGCGCGCGACGTCGCCGGAGCGGTCGAGTTCTGGACC

GACCGGCTCGGGTTCTCCCGGGACTTCGTGGAGGA

Gene Block C Design 1 Component oligonucleotide 2
(SEQ ID No. 56):
GGGTTCTCCCGGGACTTCGTGGAGGACGACTTCGCCGGTGTGGTCCGGGA

CGACGTGACCCTGTTCATCAGCGCGGTCCAGGACCAGGTAAGACGCAATT

CTGCTGTGCACGTGCCAATGCCGCTGCCCCCCAGCGCATTGGCTCACCAT

CGCCATCGCCATTG

Gene Block C Design 1 Component oligonucleotide 3
(SEQ ID No. 57):
CATTGGCTCACCATCGCCATCGCCATTGCTGCTGCAGGTGGTGCCGGACA

ACACCCTGGCCTGGGTGTGGGTGCGCGGCCTGGACGAGCTGTACGCCGAG

TGGTCGGAGGTCGTG

Gene Block C Design 1 Component oligonucleotide 4
(SEQ ID No. 58):
GTACGCCGAGTGGTCGGAGGTCGTGTCCACGAACTTCCGGGACGCCTCCG

GGCCGGCCATGACCGAGATCGGCGAGCAGCCGTGGGGCGGGAGTTCGCC

CTGCGCGACCCGGCCGGCAACTGCGTGCACTTCGTGGCCGAGGAGCAGGA

CTAAGGATCCGGATCGACGAGAGCAGCGCGACTGG

Gene Block C Design 2 Component oligonucleotide 1
(SEQ ID No. 59):
CGACACTGCTCGATCCGCTCGCACCCATATGGCCAAGCTGACCAGCGCCG
TTCC Gene Block C Design 2 Component oligonucleotide 2
(SEQ ID No. 60):
GCCAAGCTGACCAGCGCCGTTCCGGTGCTCACCGCGCGCGACGTCGCCGG

AGCGGTCGAGTTCTGGACCGACCGGCTCGGGTTCTCCCGGGACTTCGTGG

AGGACGACTTCGCCGGTGTGG

Gene Block C Design 2 Component oligonucleotide 3
(SEQ ID No. 61):
TGGAGGACGACTTCGCCGGTGTGGTCCGGGACGACGTGACCCTGTTCATC

AGCGCGGTCCAGGACCAGGTAAGACGCAATTCTGCTG

Gene Block C Design 2 Component oligonucleotide 4
(SEQ ID No. 62):
GTCCAGGACCAGGTAAGACGCAATTCTGCTGTGCACGTGCCAATGCCGCT

GCCCCCCAGCGCATTGGCTCACCATCGCCATCGCCATTGCTG

Gene Block C Design 2 Component oligonucleotide 5
(SEQ ID No. 63):
CACCATCGCCATCGCCATTGCTGCTGCAGGTGGTGCCGGACAACACCCTG

GCCTGGGTGTGGGTGCGCGGCCTGGACGAGCTGTACGCCGAGTGGTCGGA

GGTC

Gene Block C Design 2 Component oligonucleotide 6
(SEQ ID No. 64):
GCTGTACGCCGAGTGGTCGGAGGTCGTGTCCACGAACTTCCGGGACGCCT

CCGGGCCGGCCATGACCGAGATCGGCGAGCAGCC

Gene Block C Design 2 Component oligonucleotide 7
(SEQ ID No. 65):
CCATGACCGAGATCGGCGAGCAGCCGTGGGGCGGGAGTTCGCCCTGCGC

GACCCGGCCGGCAACTGCGTGCACTTCGTGGCCGAGGAGCAGGACTAAGG

Gene Block C Design 2 Component oligonucleotide 8
(SEQ ID No. 66):
CACTTCGTGGCCGAGGAGCAGGACTAAGGATCCGGATCGACGAGAGCAGC

GCGACTGG

Gene Block C Design 3 Component oligonucleotide 1
(SEQ ID No. 67):
CGACACTGCTCGATCCGCTCGCACCCATATGGCCAAGCTGACCAGCGCCG

TTCCGGTGCTCACCGCGCGCGACGTCGCCGGAGCGGTCGAGTTCTGGACC

Gene Block C Design 3 Component oligonucleotide 2
(SEQ ID No. 68):
TTCCGGTGCTCACCGCGCGCGACGTCGCCGGAGCGGTCGAGTTCTGGACC

GACCGGCTCGGGTTCTCCCGGGACTTCGTGGAGGACGACTTCGCCGGTGT

Gene Block C Design 3 Component oligonucleotide 3
(SEQ ID No. 69):
CGACCGGCTCGGGTTCTCCCGGGACTTCGTGGAGGACGACTTCGCCGGTG

TGGTCCGGGACGACGTGACCCTGTTCATCAGCGCGGTCCAGGACCAGGTA

Gene Block C Design 3 Component oligonucleotide 4
(SEQ ID No. 70):
TGGTCCGGGACGACGTGACCCTGTTCATCAGCGCGGTCCAGGACCAGGTA

AGACGCAATTCTGCTGTGCACGTGCCAATGCCGCTGCCCCCCAGCGCATT

Gene Block C Design 3 Component oligonucleotide 5
(SEQ ID No. 71):
AAGACGCAATTCTGCTGTGCACGTGCCAATGCCGCTGCCCCCCAGCGCAT

TGGCTCACCATCGCCATCGCCATTGCTGCTGCAGGTGGTGCCGGACAACA

Gene Block C Design 3 Component oligonucleotide 6
(SEQ ID No. 72):
TGGCTCACCATCGCCATCGCCATTGCTGCTGCAGGTGGTGCCGGACAACA

CCCTGGCCTGGGTGTGGGTGCGCGGCCTGGACGAGCTGTACGCCGAGTGG

Gene Block C Design 3 Component oligonucleotide 7
(SEQ ID No. 73):
ACCCTGGCCTGGGTGTGGGTGCGCGGCCTGGACGAGCTGTACGCCGAGTG

GTCGGAGGTCGTGTCCACGAACTTCCGGGACGCCTCCGGGCCGGCCATGA

Gene Block C Design 3 Component oligonucleotide 8
(SEQ ID No. 74):
GTCGGAGGTCGTGTCCACGAACTTCCGGGACGCCTCCGGGCCGGCCATGA

CCGAGATCGGCGAGCAGCCGTGGGGCGGGAGTTCGCCCTGCGCGACCCG

Gene Block C Design 3 Component oligonucleotide 9
(SEQ ID No. 75):
ACCGAGATCGGCGAGCAGCCGTGGGGGCGGGAGTTCGCCCTGCGCGACCC

GGCCGGCAACTGCGTGCACTTCGTGGCCGAGGAGCAGGACTAAGGATCCG

GATCGACGAGAGCAGCGCGACTGG

Figure 5:
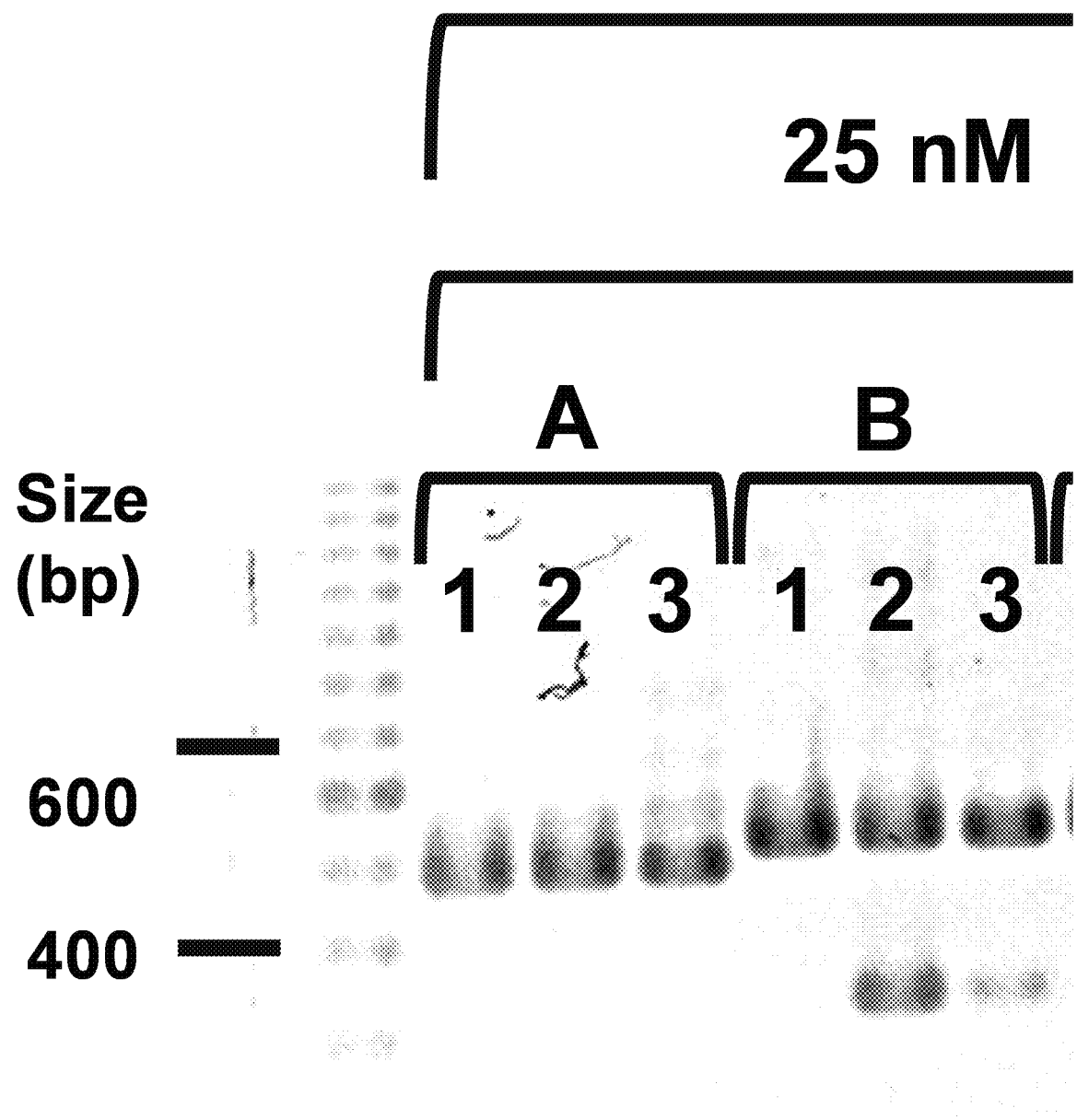
FIG. 5 is a collection of gels showing successful generation of the desired gene block assembled using varying gene sub-block designs using various sub-block concentrations.
Figure 6A:
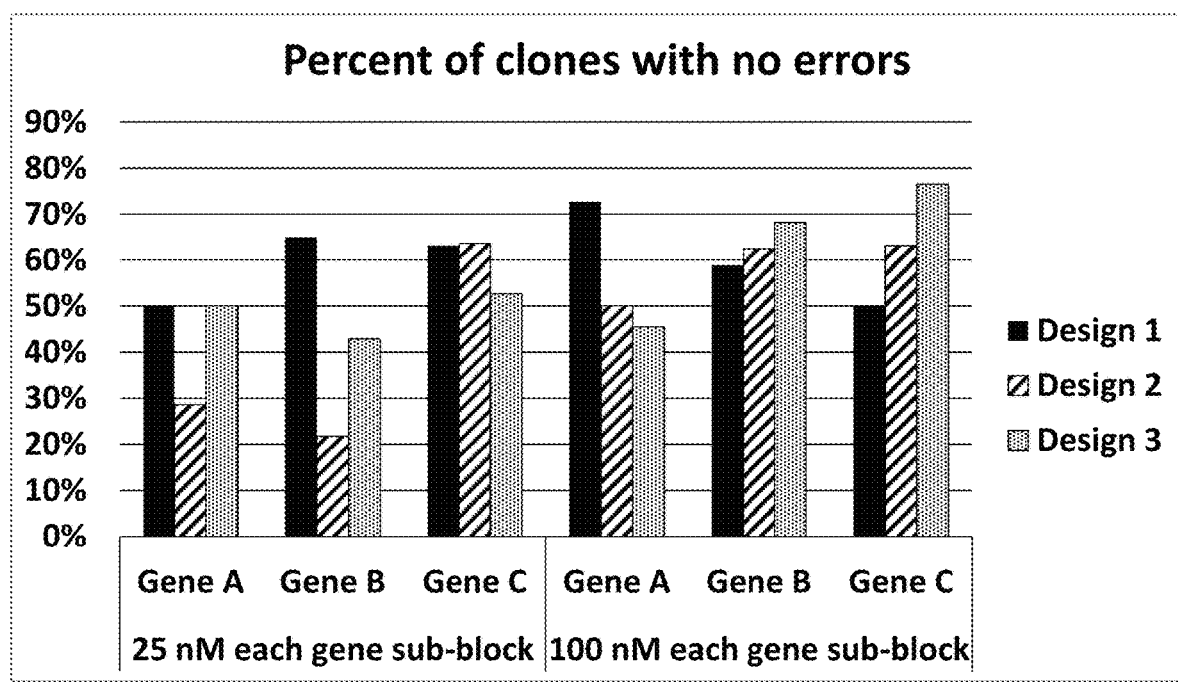
FIGS. 6A and 6B graphically represent the amount of full length clones with no errors for each set of reactions in Example 2.
Figure 6B:
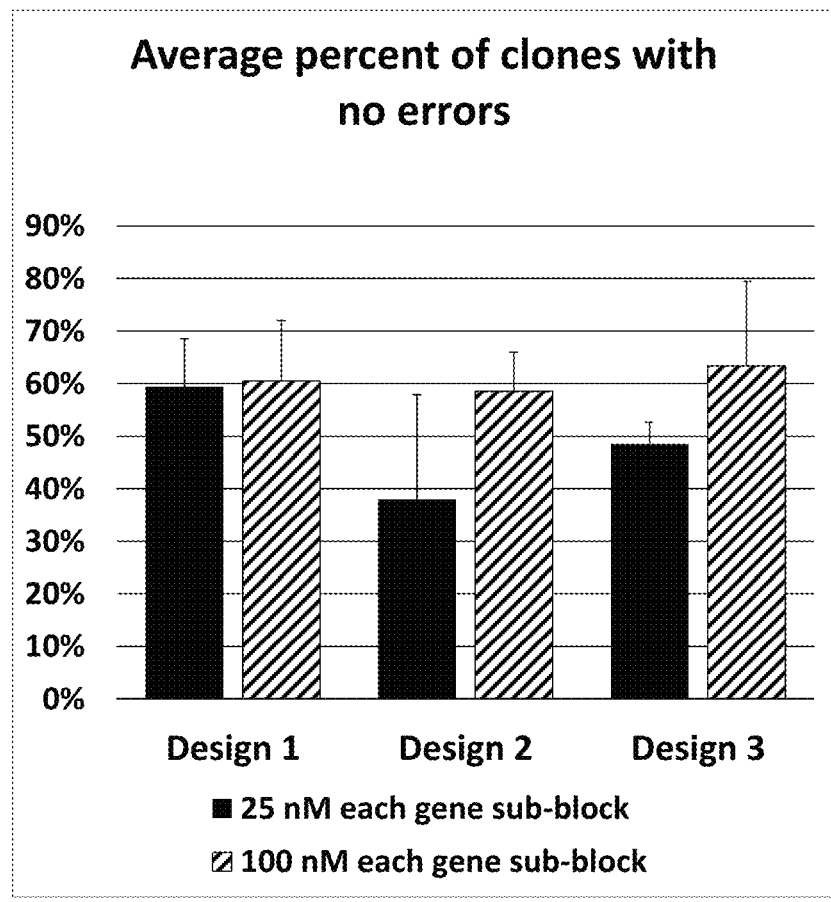

The Component oligonucleotides were pooled, assembled using TSP, diluted and subsequently amplified with PCR as was done previously in Example 1. As in Example 1, the resulting product was run on gels (see FIG. 5) and DNA sequence of the amplification product was determined for gene blocks generated using 25 nM or 100 nM of each component oligonucleotide and run for 15 TSP cycles (see FIGS. 6A and 6B). As the gels and graphs indicate, each design method, at varying cycles, produces the desired gene block product. While any of the assembly methods outlined above can be used with the method of the invention, use of the longer component oligonucleotides with less overlap is preferred to simplify design and automation as well as lowering materials cost. Thus fewer, longer component oligonucleotides can be utilized under short cycling conditions to assemble the desired gene block.

Example 3

This example demonstrates the synthesis of a gene block using TSP, followed by dilution and subsequent amplification of the desired sequence gene block from a heterogeneous assembly mixture.

Example 3 Gene Block (SEQ ID No. 76)

ACCGGTTCCTGGGCCCAGTCTGCCCTGACTCAGCCTGCCTCCGTGTCTGG

GTCTCCTGGACAGTCGATCACCATCTCCTGCAATGGAACCAGCAGTGACG

TTGGTGGATTTGACTCTGTCTCCTGGTACCAACAGCACCCAGGCAAAGCC

CCCAAACTCATGATTTATGATGTCAGTCATCGGCCCTCAGGGGTTTCTAA

TCGCTTCTCTGGCTCCAAGTCTGGCAACACGGCCTCCCTGACCATCTCTG

GGCTCCAGGCTGAGGACGAGGCTGATTATTACTGCTCTTCACTGACAGAC

AGAAGCCATCGCATATTCGGCGGAGGGACCAAGCTGACCGTCCTAGGTCA

GCCCAAGGCTGCCCCCTCGGTCACTCTGTTCCCGCCCTCGAG

Example 3 Component Oligonucleotides

SEQ ID No. 77:
CGACACTGCTCGATCCGCTCGCACCACCGGTTCCTGGGCCCAGTCTGCC

CTGACTCAGCCTGCCTCCGTGTCTGGGTCTCCTGGACAGTCGATCACCA

TCTCCTGCAATGGAACCAGCAGTGACGTTGGTGGATTTGACTCTGTCTC

CTGGTACCAACAGCACCCAGGCAAAG

-continued

SEQ ID No. 78:
CTCCTGGTACCAACAGCACCCAGGCAAAGCCCCCAAACTCATGATTTAT

GATGTCAGTCATCGGCCCTCAGGGGTTTCTAATCGCTTCTCTGGCTCCA

AGTCTGGCAACACGGCCTCCCTGACCATCTCTGGGCTCCAGGCTGAGGA

CGAG

SEQ ID No. 79:
CTCTGGGCTCCAGGCTGAGGACGAGGCTGATTATTACTGCTCTTCACTG

ACAGACAGAAGCCATCGCATATTCGGCGGAGGGACCAAGCTGACCGTCC

TAGGTCAGCCCAAGGCTGCCCCCTCGGTCACTCTGTTCCCGCCCTCGAG

GGATCGACGAGAGCAGCGCGACTGG

Forward primer (SEQ ID No. 80):
/5Phos/ACCGGTTCCTGGGCC (59.3° Tm)

Reverse Primer (SEQ ID No. 81):
/5Phos/CTCGAGGGCGGGAACAG (60.1° Tm)

There is a 29-base overlap between the first and second component oligonucleotides (70.1°Tm), and a 25-base overlap between the second and third component oligonucleotides (69.4°Tm). TSP assembly was performed on a disposable tip Janus robot, the product was then diluted (5 µl of the final product of the TSP cycling diluted into 145 µl of water), and the diluted aliquot was further amplified by PCR using the indicated terminal Forward and Reverse primers.

TSP Reaction Mixture

The TSP reaction was set up in a final reaction volume of 25 µL. Each oligonucleotide (including the forward and reverse universal primers) were at a final concentration of 140 nM in a 1×KOD DNA polymerase buffer. The reaction contained a final concentration of 0.8 mM dNTPs, 1.5 mM MgSO$_4$ and 0.5 U of KOD DNA polymerase (Novagen). The cycling parameters were: $95^{3:00}$–$(95^{0:15}$–$70^{0:30})$×30. After the initial cycling, the reaction was diluted 1:5 and was reamplified with the addition of fresh forward and reverse universal primers, MgSO$_4$, and dNTPs under the same cycling conditions.

The amplification products were separated by agarose gel electrophoresis and visualized by fluorescent dye staining to verify the length of the assembled gene block. Sample cleanup was performed (QIAquick PCR Purification Kit, Qiagen) and the product was quantified via UV absorbance (Abs=0.034, Conc.=22.1 ng/uL). Serial dilution was performed (Janus DT robot) with IDTE buffer 8.0 pH w/tRNA at a conc. 0.1 mg/ml for a final dilution of 0.3 copies/5 µL.

Serial Dilutions:
  1=5 uL of Sample, 145 µL of diluent, MIX
  2=5 uL of first dilution, 71 µL of diluent, MIX
  3=15 uL of $2^{nd}$ dilution, 145 µL of diluent, MIX
  4=15 uL of $3^{rd}$ dilution, 145 µL of diluent, MIX
  5=15 uL of $4^{th}$ dilution, 145 µL of diluent, MIX
  6=15 uL of $5^{th}$ dilution, 145 µL of diluent, MIX
  7=15 uL of $6^{th}$ dilution, 145 µL of diluent, MIX
  8=15 uL of $7^{th}$ dilution, 145 µL of diluent, MIX
  9=15 uL of $8^{th}$ dilution, 145 µL of diluent, MIX
  10=15 uL of $9^{th}$ dilution, 145 µL of diluent, MIX
  11=15 uL of $10^{th}$ dilution, 145 µL of diluent, MIX Dilution PCR: Plates containing 1×KOD buffer, 0.25 U KOD DNA polymerase, 1.5 mM MgSO$_4$, 300 nM forward and reverse universal primers, and 0.6× EvaGreen, 5 µL of the final dilution of the assembled gene block, all in a final volume of 25 µL. The cycling conditions were $95^{2:00}$–$(95^{0:20}$–$70^{1:00})$×45.

Wells containing a positive fluorescent signal were diluted 1:16 in water. The diluted amplified product was then sequence verified using standard Sanger based sequencing on a 3730XL DNA sequencer. One µL of the diluted clonally amplified product was further amplified by PCR using gene specific terminal primers under the following conditions; 1×KOD buffer, 0.5 U KOD DNA polymerase, 1.5 mM MgSO$_4$, 0.8 mM dNTPs, and 200 nM primers. The cycling conditions were $95^{3:00}$–$(95^{0:15}$–$60^{0:15}$–$70^{0:30})$×30 cycles.

Figure 7:
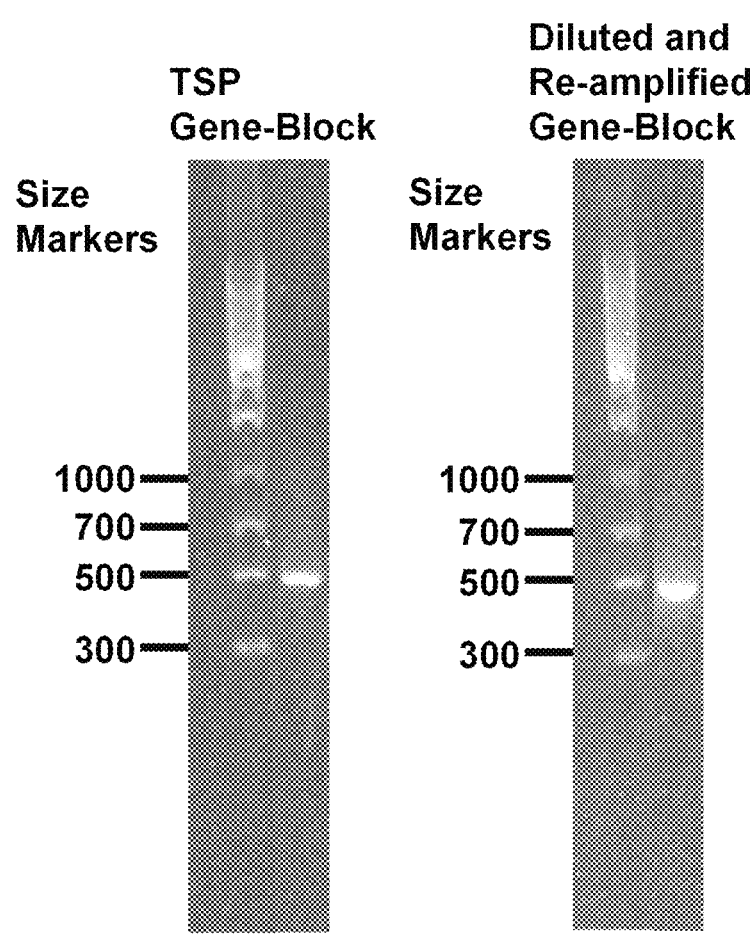
FIG. 7 is a gel showing a successful synthesis and assembly of a gene block as described in Example 3.

The TSP generated gene block and dilution-amplified gene block were separated using agarose gel electrophoresis and visualized by fluorescent dye staining. A 1 kb marker size ladder (Axygen) was included (see FIG. 7). The size markers are shown for the four smallest standards. The expected product is 442 bp, and products of this size were visualized on the gel.

Example 4

The present example demonstrates an alternate protocol wherein the TSP cycling conditions are modified to allow for longer extension times to make longer gene blocks. The longer cycling conditions significantly improve the resulting desired product.

The 8 sub-block gene block (1155 bases, SEQ ID No. 2) from Example 1 was synthesized, as well as a 10 sub-block gene block (1308 bases, SEQ ID No. 82). The 10 sub-blocks are SEQ ID Nos. 83-92.

Figure 8:
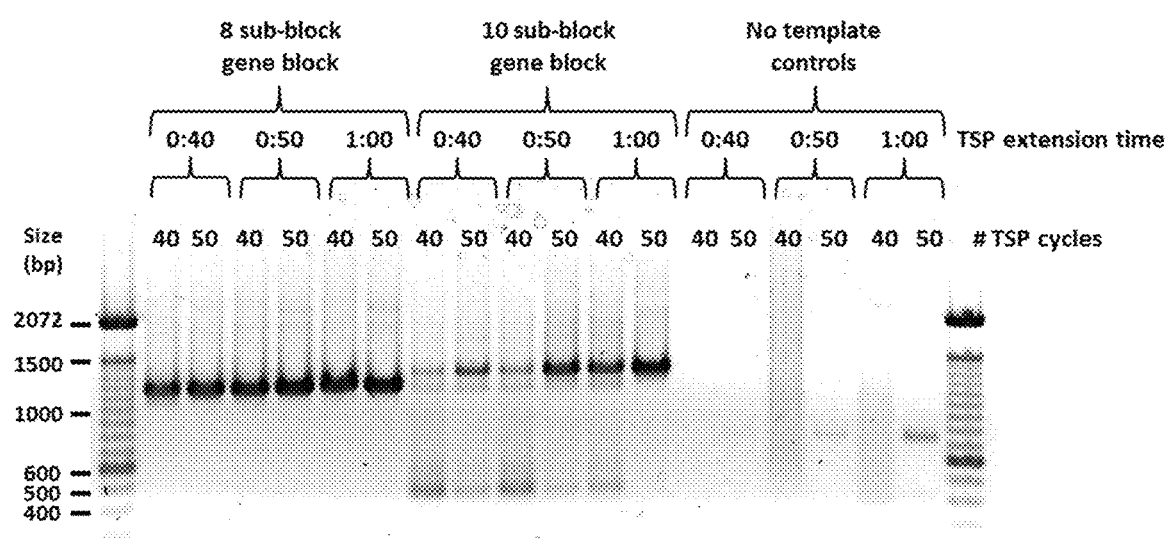
FIG. 8 is a gel showing a successful synthesis and assembly of an 8 sub-block gene block and a 10 sub-block gene block as described in Example 4.

The component oligonucleotides were assembled by TSP using the following reaction mixture and conditions:
50 nM component oligonucleotides
50 nM forward primer
200 nM reverse primer
0.02 U/uL KOD Hot-Start DNA polymerase (Novagen)
1× buffer for KOD Hot Start DNA polymerase (Novagen)
1.5 mM MgSO$_4$
0.8 mM dNTPs (0.2 mM each)
Cycling conditions: 95° C.$^{3:00}$ (95° C.$^{0:20}$–70° C.$^{0:40,\ 0:50,\ 1:00}$)×40 or 50 cycles After the TSP cycles, the resulting products were diluted 100-fold in water, and then underwent a further step of PCR containing 200 nM each of the universal forward primer and 200 nM of the universal reverse primer (cycling conditions: 95° C.$^{3:00}$ (95° C.$^{0:20}$–70° C.$^{0:40}$)×30 cycles). The resulting gene block was run on a 1% agarose gel at 100V for 1 hour 15 minutes (see FIG. 8). The expected products were 1155 bp and 1308 bp respectively, and products of these sizes were visualized on the gel.

SEQ ID No. 82: 10 sub-block gene block
CGACACTGCTCGATCCGCTCGCACCCCGCCTTGTTTAACTTTAAGAAGGA

GCCCTTCCCCATGACAAGAACAAGTTTGCCTTTTCCAGACGGTTTCCTGT

GGGGCGCAAGCACGGCGGCTCACCAGATTGAAGGTAATAATGTAAATAGT

GATTGGTGGAGAAAAGAACATGACCCTGCTGCAAATATTGCAGAACCATC

TTTGGATGCCTGTGACTCATATCACCGCTGGGAACAAGATATGGACCTGT

TAGCAGAACTGGGCTTTACCGATTACCGCTTCTCCGTTGAATGGGCCCGT

ATTGAACCTGTGCCAGGTACATTTTCGCATGCTGAAACGGCACACTATCG

TAGAATGGTTGATGGTGCTTTGGCAAGAGGCCTGCGCCCAATGGTCACCC

TGCATCACTTTACTGTACCGCAGTGGTTCGAAGATTTGGGTGGCTGGACA

GCCGATGGTGCCGCGGACCTGTTTGCACGTTACGTCGAACATTGTGCTCC

-continued

GATTATCGGTAAAGATGTTAGACACGTGTGCACGATTAATGAACCTAACA

TGATCGCCGTAATGGCGGGCTTAGCTAAGACAGGCGATCAAGGTTTCCCA

CCGGCGGGTTTGCCTACGCCTGACGAAGAAACCACTCATGCTGTTATTGC

TGCACATCACGCCGCGGTCAAAGCAGTACGTGCCATTGATCCGGACATCC

AGGTCGGCTGGACCATCGCTAATCAAGTATATCAGGCATTACCTGGTGCC

GAAGATGTTACTGCTGCATATCGTTACCCAAGAGAAGACGTGTTCATTGA

AGCCGCTCGTGGCGATGACTGGATCGGCGTGCAATCTTACACACGCACGA

AGATTGGTGCGGATGGCCCAATCCCGGCGCCTGAAGACGCTGAACGCACC

CTGACTCAGTGGGAATATTACCCAGCTGCTGTTGGTCATGCTCTGCGTCA

CACAGCGGATGTCGCTGGCCCAGACATGCCGTTAATTGTAACCGAAAACG

GTATCGCCACTGCGGATGACGCACGCCGTGTGGATTATTACACTGGTGCA

CTGGAAGCCGTTTCAGCCGCGTTAGAAGATGGTGTGAATATTCATGGCTA

TCTGGCGTGGAGCGCTTTGGATAACTATGAATGGGGTAGTTACAAACCGA

CTTTTGGCCTGATCGCAGTTGATCCTGTGACATTCGAAAGAACGGCCAAG

CCGTCAGCAGTGTGGTTAGGTGAAATGGGTAGAACAAGACAGTTGCCAAG

AGCGGAACGCGGGAAGGGTGGGCGCGCCGACCCGGATCGACGAGAGCAGC

GCGACTGG

Sub-block sequences:
SEQ ID No. 83:
CGACACTGCTCGATCCGCTCGCACCCCGCCTTGTTTAACTTTAAGAAGGA

GCCCTTCCCCATGACAAGAACAAGTTTGCCTTTTCCAGACGGTTTCCTGT

GGGGCGCAAGCACGGCGGCTCACCAGATTGAAGGTAATAATGTAAATAGT

GATTGGTGGAG

SEQ ID No. 84:
GCTCACCAGATTGAAGGTAATAATGTAAATAGTGATTGGTGGAGAAAAGA

ACATGACCCTGCTGCAAATATTGCAGAACCATCTTTGGATGCCTGTGACT

CATATCACCGCTGGGAACAAGATATGGACCTGTTAGCAGAACTGGGCTTT

ACCGATTACCGCTTCTCCGTTG

SEQ ID No. 85:
GAACTGGGCTTTACCGATTACCGCTTCTCCGTTGAATGGGCCCGTATTGA

ACCTGTGCCAGGTACATTTTCGCATGCTGAAACGGCACACTATCGTAGAA

TGGTTGATGGTGCTTTGGCAAGAGGCCTGCGCCCAATG

SEQ ID No. 86:
CTTTGGCAAGAGGCCTGCGCCCAATGGTCACCCTGCATCACTTTACTGTA

CCGCAGTGGTTCGAAGATTTGGGTGGCTGGACAGCCGATGGTGCCGCGGA

CCTGTTTGCACGTTACGTCGAACATTGTGCTCCGATTATCGGTAAAGATG

TTAGACAC

SEQ ID No. 87:
GTCGAACATTGTGCTCCGATTATCGGTAAAGATGTTAGACACGTGTGCAC

GATTAATGAACCTAACATGATCGCCGTAATGGCGGGCTTAGCTAAGACAG

GCGATCAAGGTTTCCCACCGGCGGGTTTGCCTACGCCTGACGAAGAAACC

AC

SEQ ID No. 88:
GGGTTTGCCTACGCCTGACGAAGAAACCACTCATGCTGTTATTGCTGCAC

ATCACGCCGCGGTCAAAGCAGTACGTGCCATTGATCCGGACATCCAGGTC

GGCTGGACCATCGCTAATCAAGTATATCAGGCATTACCTGGTGCCGAAGA

TGTTACTG

SEQ ID No. 89:
ATCAGGCATTACCTGGTGCCGAAGATGTTACTGCTGCATATCGTTACCCA

AGAGAAGACGTGTTCATTGAAGCCGCTCGTGGCGATGACTGGATCGGCGT

GCAATCTTACACACGCACGAAGATTGGTGCGGATGGCCCAATCCCGGCGC

CTGAAGACGCTGAACGCACCCTGACTCAGTGGGAATATTACCC

SEQ ID No. 90:
CTGAACGCACCCTGACTCAGTGGGAATATTACCCAGCTGCTGTTGGTCAT

GCTCTGCGTCACACAGCGGATGTCGCTGGCCCAGACATGCCGTTAATTGT

AACCGAAAACGGTATCGCCACTGCGGATGACGCACGCCGTGTGGATTATT

ACACTGGTGCACTGGAAGCCGTTTCAGCCGCGTTA

SEQ ID No. 91:
GCACTGGAAGCCGTTTCAGCCGCGTTAGAAGATGGTGTGAATATTCATGG

CTATCTGGCGTGGAGCGCTTTGGATAACTATGAATGGGGTAGTTACAAAC

CGACTTTTGGCCTGATCGCAGTTGATCCTGTGACATTCGAAAGAACGGCC

AAG

SEQ ID No. 92:
CAGTTGATCCTGTGACATTCGAAAGAACGGCCAAGCCGTCAGCAGTGTGG

TTAGGTGAAATGGGTAGAACAAGACAGTTGCCAAGAGCGGAACGCGGGAA

GGGTGGGCGCGCCGACCCGGATCGACGAGAGCAGCGCGACTGG

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A gene fragment library, said library comprising: a plurality of non-vector synthetic nucleic acid gene fragments wherein two or more of the gene fragments are comprised of a constant gene block$_a$ of at least 100 bases and a variable gene block of at least 50 bases, wherein the constant gene block sequence is identical for each of the gene fragments and the variable gene block sequence varies, and wherein the plurality of non-vector synthetic nucleic acid gene fragments are chemically synthesized.

2. The gene fragment library of claim 1 wherein the gene fragments further comprise constant gene block$_b$.

3. The gene fragment library of claim 2 wherein the variable gene block is flanked by constant gene block$_a$ and constant gene block$_b$.

4. The gene fragment library of claim 2 wherein the gene fragments further comprise constant gene block$_n$ wherein n represents a plurality of sets of constant gene blocks.

5. The gene fragment library of claim 1 wherein the gene fragments further comprise variable gene block$_n$ wherein n represents a plurality of sets of variable gene blocks.

6. The gene fragment library of claim 1 wherein the gene fragments are at least 400 bases.

7. The gene fragment library of claim 1 wherein the gene fragments are at least 1000 bases.

8. The gene fragment library of claim 3 wherein the constant gene blocks located on terminal ends contain a binding site for a forward primer on a first gene block located at a first terminal end and a reverse amplification primer on a second gene block located at a second terminal end.

9. The gene fragment library of claim 1 wherein the constant gene blocks and the variable gene blocks contain overlap regions for assembly into a gene fragment.

10. The gene fragment library of claim 9 wherein the overlap regions contain a same sequence of complementarity that allow for assembly with universal primers.

* * * * *